US010470688B2

(12) United States Patent
Fujimoto

(10) Patent No.: US 10,470,688 B2
(45) Date of Patent: Nov. 12, 2019

(54) MEASUREMENT APPARATUS, METHOD AND NON-TRANSITORY COMPUTER-READABLE RECORDING MEDIUM

(71) Applicant: FUJITSU LIMITED, Kawasaki-shi, Kanagawa (JP)

(72) Inventor: Hiroaki Fujimoto, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 265 days.

(21) Appl. No.: 15/447,511

(22) Filed: Mar. 2, 2017

(65) Prior Publication Data
US 2017/0251953 A1 Sep. 7, 2017

(30) Foreign Application Priority Data
Mar. 7, 2016 (JP) .................. 2016-043731

(51) Int. Cl.
*G06K 9/00* (2006.01)
*A61B 5/107* (2006.01)
*A61B 5/00* (2006.01)

(52) U.S. Cl.
CPC .......... *A61B 5/1071* (2013.01); *A61B 5/1079* (2013.01); *A61B 5/7267* (2013.01); *A61B 5/7278* (2013.01)

(58) Field of Classification Search
CPC ... A61B 5/1071; A61B 5/1079; A61B 5/7267; A61B 5/727
See application file for complete search history.

(56) References Cited

U.S. PATENT DOCUMENTS

| 7,254,253 B2 * | 8/2007 | Higaki ............... G06K 9/00335 382/103 |
| 9,327,399 B2 * | 5/2016 | Doi ...................... B62D 57/032 |
| 2012/0310075 A1 | 12/2012 | Russell |
| 2013/0243259 A1 | 9/2013 | Kawaguchi et al. |
| 2015/0003687 A1 | 1/2015 | Utsunomiya et al. |
| 2015/0320343 A1 | 11/2015 | Utsunomiya et al. |

(Continued)

FOREIGN PATENT DOCUMENTS

| JP | 2014-068714 | 4/2014 |
| JP | 2014-136137 | 7/2014 |

(Continued)

OTHER PUBLICATIONS

Jamie Shotton et al., "Real-Time Human Pose Recognition in Parts from Single Depth Images," In Proc. CVPR, 2011, 8 pages.

(Continued)

*Primary Examiner* — Tom Y Lu
(74) *Attorney, Agent, or Firm* — Staas & Halsey LLP

(57) ABSTRACT

A measurement apparatus which includes a processor is provided. The processor is configured to calculate, based on a distance image of a measurement target object with at least a joint, a position of a first portion of the measurement target object which corresponds to a non-joint portion or a terminal portion, and a position of a second portion of the measurement target object different from the first portion, and calculate, based on a first line connecting the calculated positions, a joint angle related to a joint of a first measurement target of the measurement target object.

15 Claims, 26 Drawing Sheets

(56) References Cited

U.S. PATENT DOCUMENTS

2015/0325004 A1* 11/2015 Utsunomiya .......... A61B 5/742
                                                        382/103

FOREIGN PATENT DOCUMENTS

JP          2015-61579      4/2015
WO          2012/077286     6/2012

OTHER PUBLICATIONS

Jamie Shotton et al., "Efficient Human Pose Estimation from Single Depth Images," (Invited Paper—CVPR 2011 special issue), pp. 1-21.
J-Plat-Pat English Language Abstract for JP 2014-068714, published Apr. 21, 2014.
J-Plat-Pat English Language Abstract for JP 2014-136137, published Jul. 28, 2014.
Patent Abstracts of Japan English abstract for Japanese Patent Publication No. 2015-61579, published Apr. 2, 2015.
Japanese Office Action dated Sep. 10, 2019 in corresponding Japanese Patent Publication No. 2016-043731.

* cited by examiner

FIG.12

| No. | PORTION NAME | MOTION DIRECTION | PARTICULAR MEASUREMENT ITEM |
|---|---|---|---|
| 1 | SHOULDER BLADE | FLEXION/EXTENSION | × |
| 2 | | ELEVATION/DEPRESSION | × |
| 3 | SHOULDER | FLEXION/EXTENSION | ○ |
| 4 | | ABDUCTION/ADDUCTION | ○ |
| 5 | | EXTERNAL ROTATION/ INTERNAL ROTATION | ○ |
| 6 | | HORIZONTAL FLEXION/ HORIZONTAL EXTENSION | ○ |
| 7 | ELBOW | FLEXION/EXTENSION | × |
| 8 | FOREARM | PRONATION/SUPINATION | × |
| 9 | WRIST | FLEXION/EXTENSION | × |
| 10 | | RADIAL DEVIATION/ ULNAR DEVIATION | × |
| 11 | THUMB | RADIAL ABDUCTION/ ULNAR ADDUCTION | × |
| 12 | | PALMAR ABDUCTION/ PALMAR ADDUCTION | × |
| 13 | | FLEXION/EXTENSION | × |
| 14 | | FLEXION/EXTENSION | × |
| 15 | FINGER | FLEXION/EXTENSION | × |
| 16 | | FLEXION/EXTENSION | × |
| 17 | | FLEXION/EXTENSION | × |
| 18 | | ABDUCTION/ADDUCTION | ○ |
| 19 | HIP | FLEXION/EXTENSION | × |
| 20 | | ABDUCTION/ADDUCTION | ○ |
| 21 | | EXTERNAL ROTATION/ INTERNAL ROTATION | ○ |
| 22 | KNEE | FLEXION/EXTENSION | × |

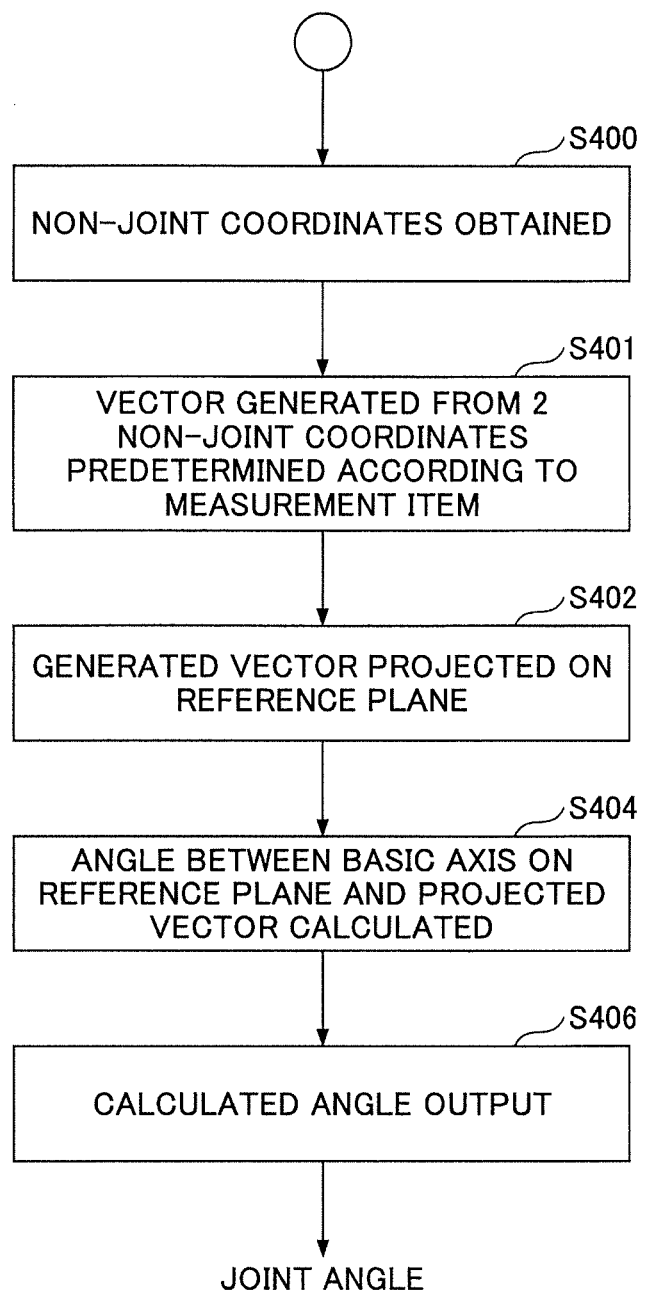

MEASUREMENT APPARATUS, METHOD AND NON-TRANSITORY COMPUTER-READABLE RECORDING MEDIUM

CROSS-REFERENCE TO RELATED APPLICATIONS

This present application is based upon and claims the benefit of priority of the prior Japanese Patent Application No. 2016-043731, filed on Mar. 7, 2016, the entire contents of which are incorporated herein by reference.

FIELD

The disclosure is related to a measurement apparatus, a measurement method, and a non-transitory computer-readable recording medium.

BACKGROUND

A technique is known from NON-Patent document no. 1, for example, in which portions of a human body are recognized based on a distance image (depth image) of the human body to localize joint positions of the human body.

However, according to the prior art as described above, it is difficult to increase accuracy of the calculated joint positions, because the joint portions in the distance image are smaller in size than non-joint portions. It is difficult to calculate a joint angle with high accuracy based on the joint positions calculated with decreased accuracy.

[Non-Patent Document 1] "Real-time human pose recognition in parts from a single depth images" by J. Shotton, A. Fitzgibbon, M. Cook, T. Sharp, M. Finocchio, R. Moore, A. Kipman, and A. Blake, In Proc. CVPR, 2011".

[Patent Document 1] International Publication Pamphlet No. WO2012/077286

[Patent Document 2] Japanese Laid-open Patent Publication No. 2014-68714

[Patent Document 3] Japanese Laid-open Patent Publication No. 2014-136137

SUMMARY

According to one aspect, a measurement apparatus is provided, which includes a processor.
The processor is configured to:
calculate, based on a distance image of a measurement target object with at least a joint, a position of a first portion of the measurement target object which corresponds to a non-joint portion or a terminal portion, and a position of a second portion of the measurement target object different from the first portion, and
calculate, based on a first line connecting the calculated positions, a joint angle related to a joint of a first measurement target of the measurement target object.

The object and advantages of the embodiment will be realized and attained by means of the elements and combinations particularly pointed out in the claims. It is to be understood that both the foregoing general description and the following detailed description are exemplary and explanatory and are not restrictive of the invention.

BRIEF DESCRIPTION OF DRAWINGS

FIG. 12 is a table illustrating an example of measurement items.

FIG. 14B is a flowchart illustrating an example of a joint angle calculation way by a particular joint angle calculation part.

DESCRIPTION OF EMBODIMENTS

In the following, embodiments are described in detail with reference to appended drawings.

Figure 1:
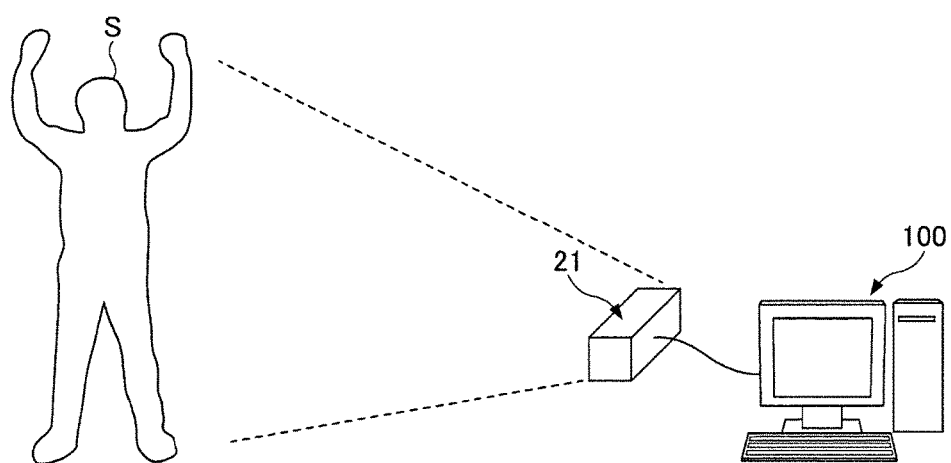
FIG. 1 is a diagram schematically illustrating a configuration of a ROM (Range Of Motion) measurement apparatus according to an example.

FIG. 1 is a diagram schematically illustrating a configuration of a ROM measurement apparatus 1 according to an example. In FIG. 1, a test subject S (an example of a measurement target object) is illustrated for explanation purpose.

The ROM measurement apparatus 1 includes a distance image sensor 21 and a processing device 100.

The distance image sensor 21 obtains a distance image of the test subject S. For example, the distance image sensor 21 is a three-dimensional image sensor that performs sensing for a space as a whole to measure distances, thereby obtaining the distance image that includes distance information on a pixel basis like a digital image. A way of obtaining the distance information is arbitrary. For example, the way of obtaining the distance information is based on an active stereo type in which a projection of a particular pattern on a target is sensed by an image sensor, and the distance information is obtained with triangulation based on a geometrical distortion in the particular pattern. Further, the way of obtaining the distance information is based on a TOF (Time-of-Flight) type in which laser light is emitted, and reflection light is sensed by an image sensor to measure the distance based on phase shift information.

It is noted that the distance image sensor 21 may be provided in a fixed manner or in a movable manner. Further, a plurality of distance image sensors 21 may be used. For example, if a plurality of distance image sensors 21 are used, the distance image sensor 21 to be used may be changed according to a measurement item (described hereinafter). Further, if the distance image sensor 21 is provided in a movable way, the position of the distance image sensor 21 may be changed according to the measurement item (described hereinafter).

Figure 2:
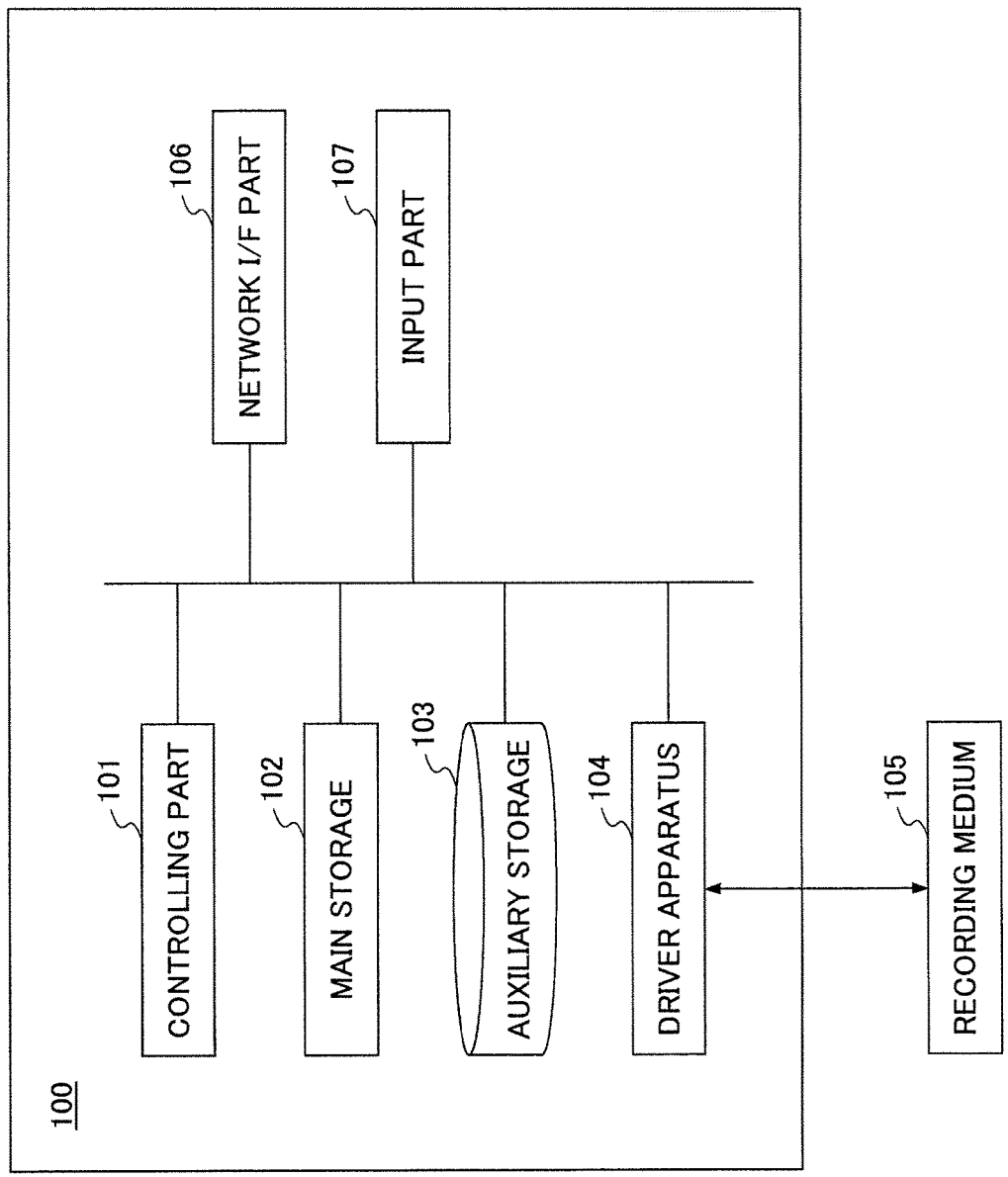
FIG. 2 is a diagram illustrating an example of a hardware resource configuration of a processing device.

FIG. 2 is a diagram illustrating an example of a hardware resource configuration of the processing device 100.

As illustrated in FIG. 2, the processing device 100 includes a controlling part 101, a main storage 102, an auxiliary storage 103, a driver apparatus 104, a network I/F part 106, and an input part 107.

The controlling part 101 is an arithmetical unit which executes programs stored in the main storage 102 or the auxiliary storage 103. The controlling part 101 receives the data from the input part 107 or the storage and outputs to the storage after performing the calculation or processing.

The main storage 102 is a ROM (Read Only Memory), a RAM (Random Access Memory) or the like. The main storage 102 stores or temporarily store programs such as an OS, which is fundamental software the controlling part 101 executes, or application software or data.

The auxiliary storage 103 is a HDD (Hard Disk Drive) or the like. The auxiliary storage 103 stores data related to the application software, etc.

The driver apparatus 104 reads the programs from a recording medium 105, for example, a flexible disk, and installs the programs in the storage.

The recording medium 105 stores a predetermined program. The program stored in the recording medium 105 is installed in the processing device 100 via the driver apparatus 104. The installed program can be executed by the processing device 100.

The network I/F part 106 is an interface between peripherals with communication capabilities, which are connected via a network constructed by data transmission lines such as wired and/or wireless transmission lines, and the processing device 100.

The input device 107 may include a keyboard including cursor keys, number keys and function keys, a mouse, a touch pad or the like. The input device 107 may be adapted for other input ways such as a speech input, a gesture input, etc.

It is noted that, in the example illustrated in FIG. 2, the processes described hereinafter can be implemented by causing the processing device 100 to execute one or more programs. Further, it is also possible to store one or more programs in the recording medium 105, and cause the processing device 100 to read the programs stored in the recording medium 105 to implement the processes described hereinafter. It is noted that the recording medium 105 may be of any type. For example, the recording medium 105 may include a recording medium for optically, electrically or magnetically storing information, such as a CD-ROM, a flexible disk, a magneto-optical disk, and a semiconductor memory for electrically storing information, such as a ROM, a flash memory, etc. It is noted that carrier waves are not included in a concept of the term "recording medium".

Figure 3:
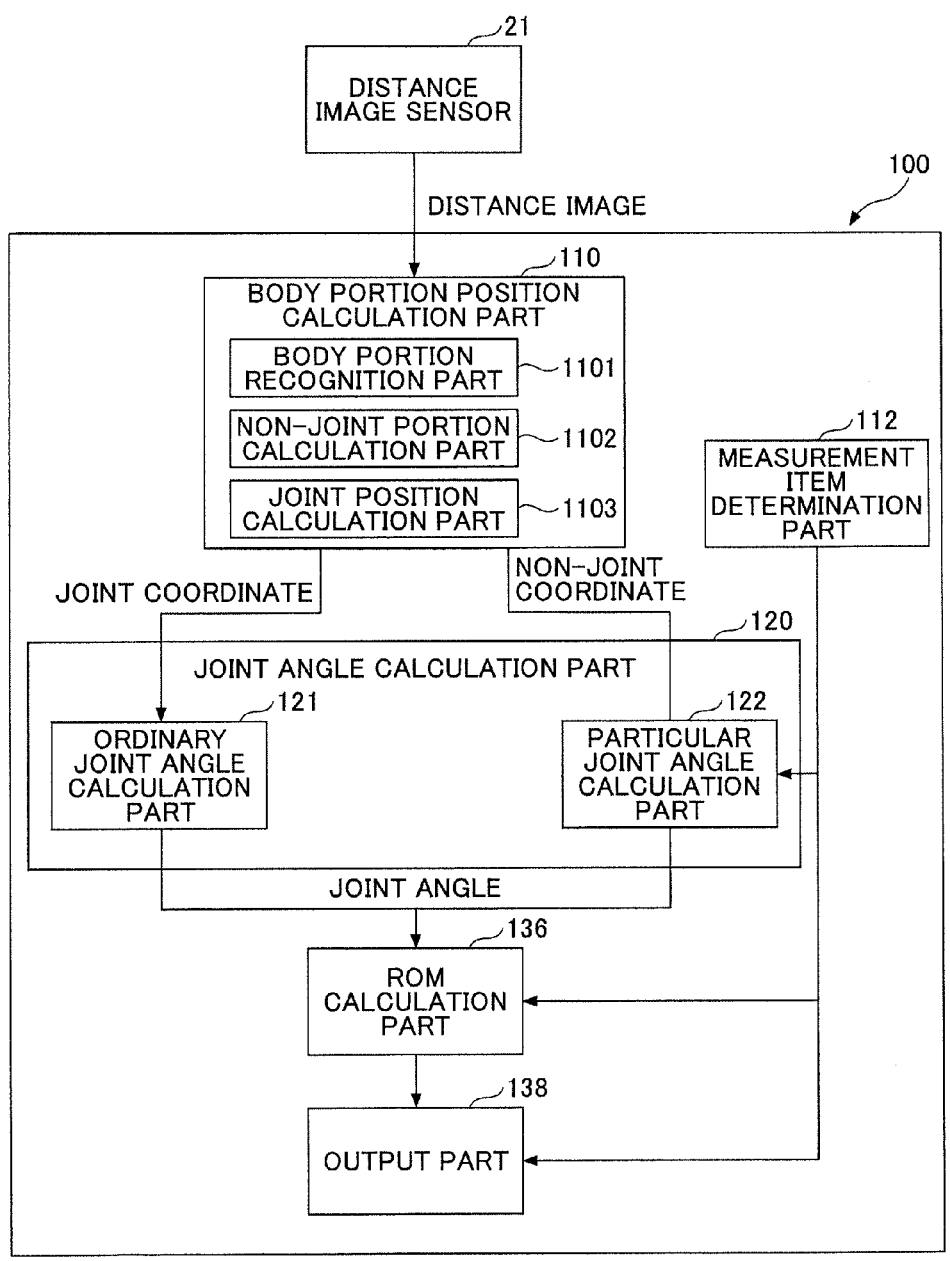
FIG. 3 is a block diagram illustrating an example of functions of the processing device.

FIG. 3 is a block diagram of an example of a configuration of the processing device 100. In FIG. 3, the distance image sensor 21 that inputs the distance image to the processing device 100 is also illustrated.

In the example illustrated in FIG. 3, the processing device 100 includes a body portion position calculation part 110, a measurement item determination part 112, a joint angle calculation part 120, a ROM calculation part 136, and an output part 138. The joint angle calculation part 120 includes an ordinary joint angle calculation part 121, and a particular joint angle calculation part 122. The body portion position calculation part 110, the measurement item determination part 112, the joint angle calculation part 120, and the output part 138 can be implemented by the controlling part 101 executing one or more programs stored in the main storage 102 illustrated in FIG. 2.

The body portion position calculation part 110 includes a body portion recognition part 1101, a non-joint portion calculation part 1102, and a joint position calculation part 1103.

To the body portion recognition part 1101 is input the distance image of the test subject S from the distance image sensor 21. The body portion recognition part 1101 recognizes the portions of the human body of the test subject S in the distance image. The recognition of the portions of the human body can be implemented by a learning result obtained by machine learning in advance. An example of recognizing the portions of the human body is described hereinafter with reference to FIG. 5 through FIG. 7.

Figure 4:
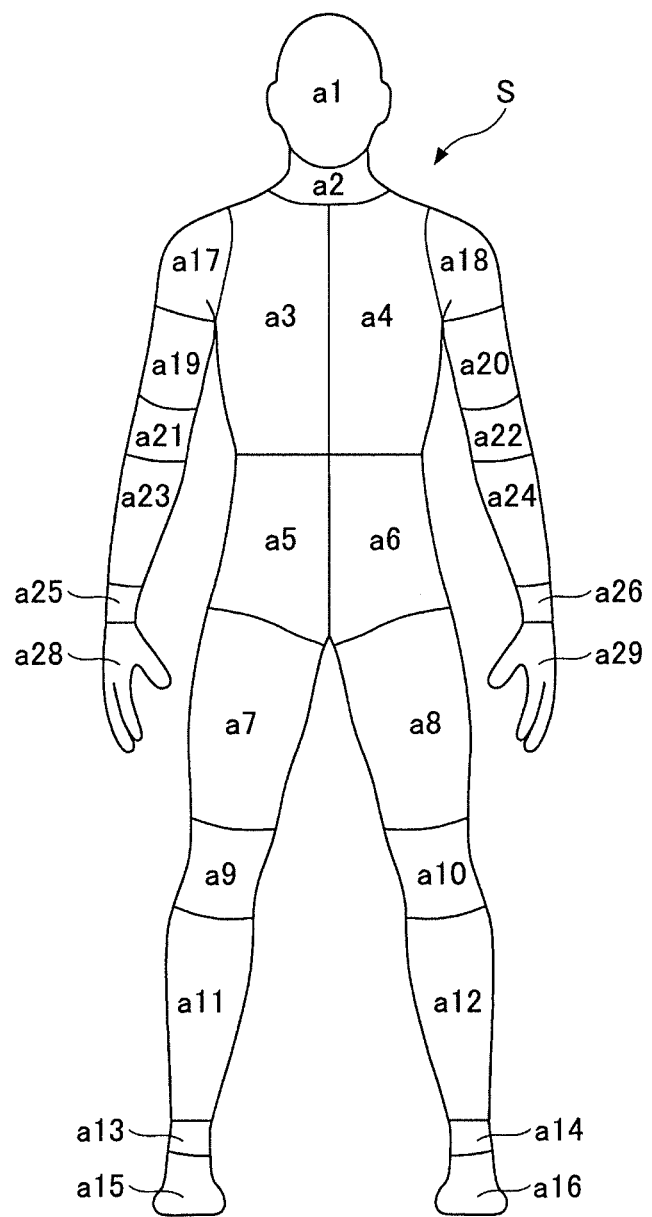
FIG. 4 is a diagram illustrating an example of a way of portioning a human body.

FIG. 4 is a diagram illustrating an example of a way of portioning the human body. In the example illustrated in FIG. 4, the human body is divided into 29 portions a1 through a29, as an example. The human body includes joint portions (a17, a18, a21, a22, etc., for example), non-joint portions (a19, a20, a23, a24, etc., for example), and terminal (distal) portions of arms and feet (a15, a16, a28, a29). The respective portions of the human body thus assigned may be given unique labels, for example. In the following, recognizing the portions of the human body (the portions of the human body to which the labels are given) is referred to as "labeling".

Figure 5:
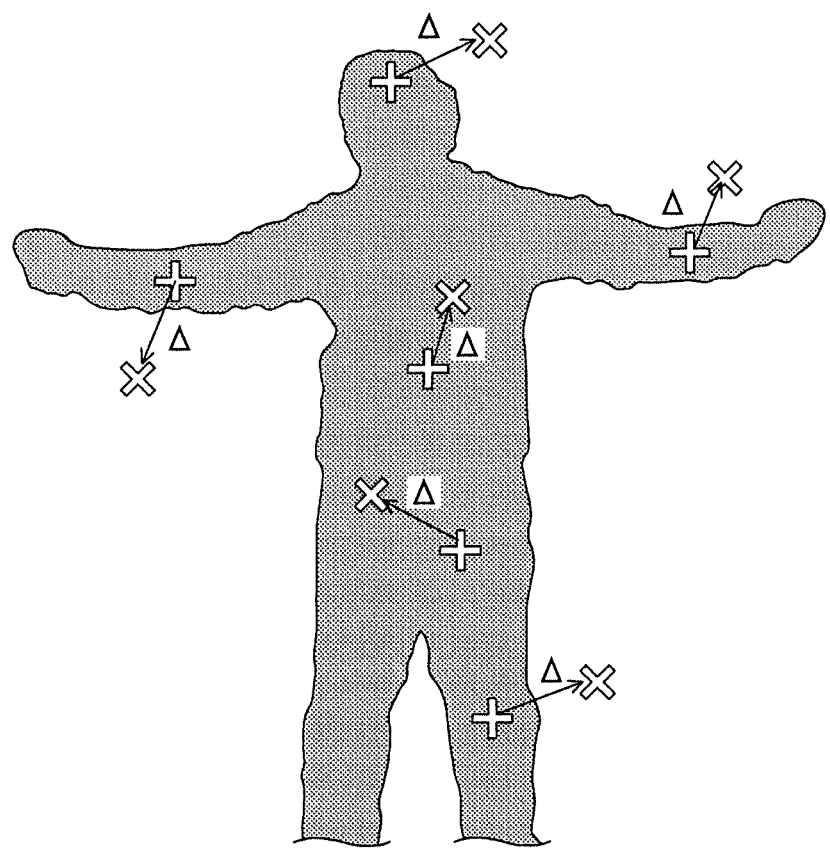
FIG. 5 is a conceptual diagram of target points and offset points in a distance image.
Figure 6:
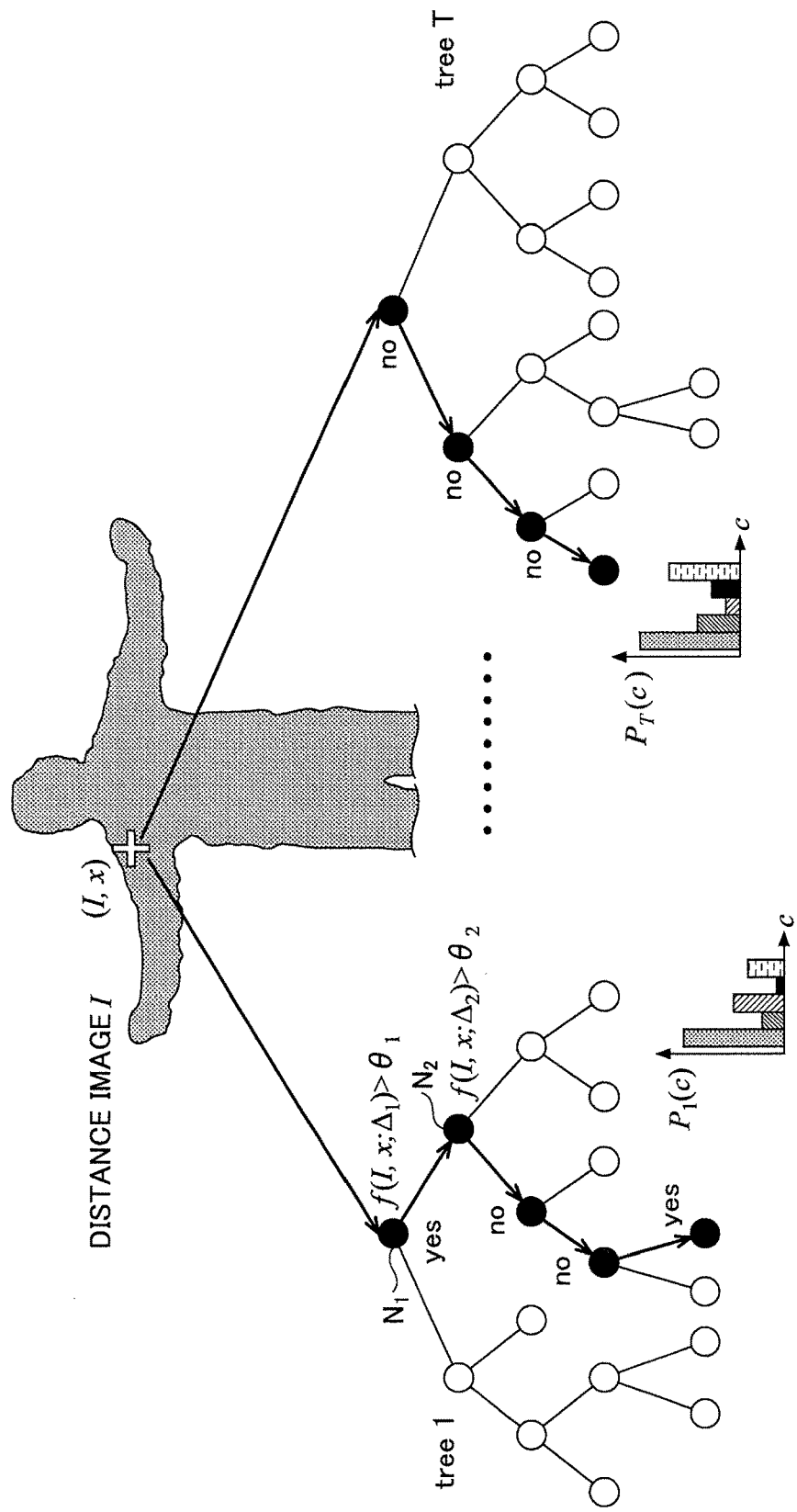
FIG. 6 is a diagram explaining a way of recognizing body portions using a decision tree on a pixel basis.
Figure 7:
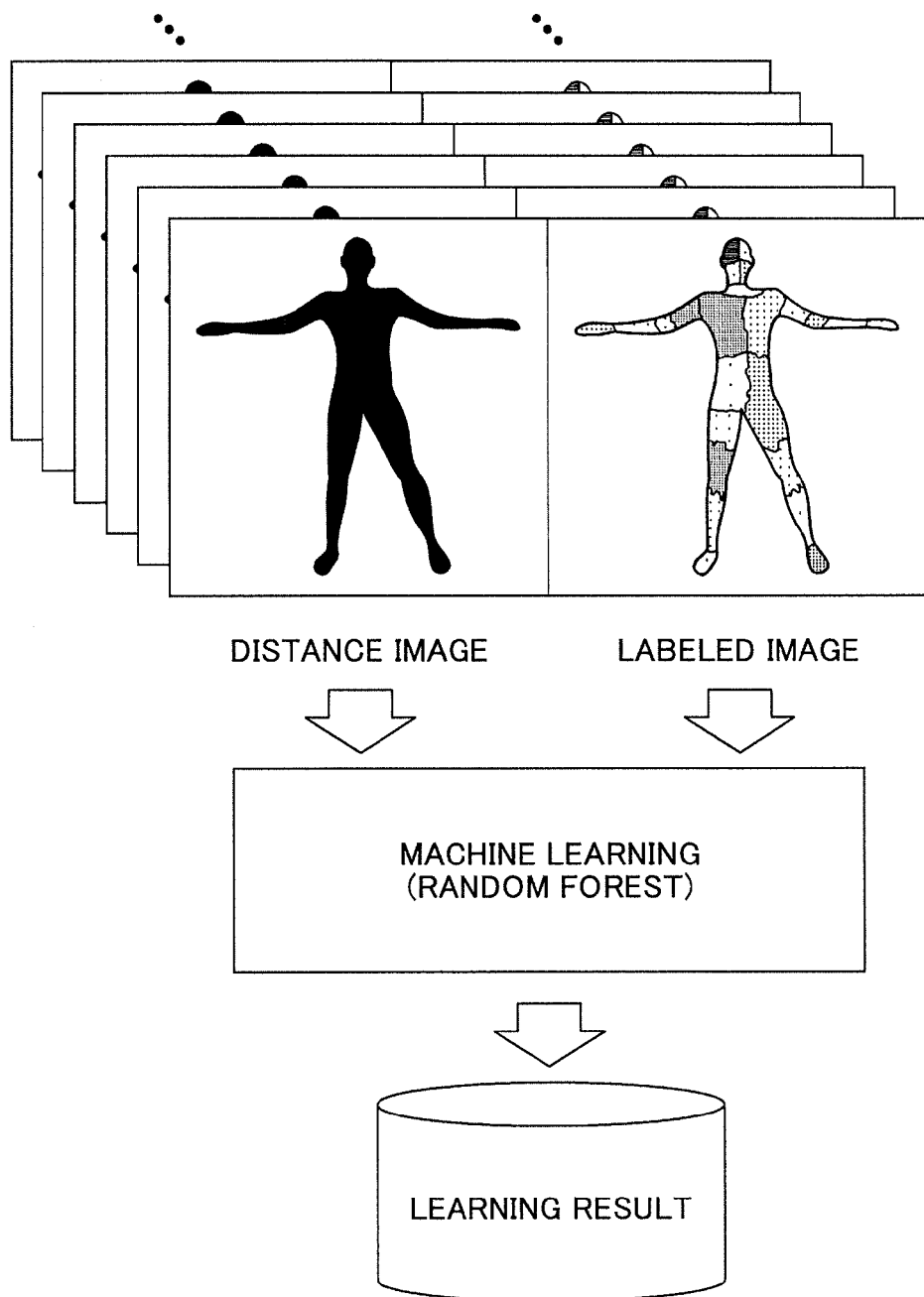
FIG. 7 is a diagram illustrating an overview of machine learning.

Here, with reference to FIG. 5 through FIG. 7, an example of a way of recognizing the portions of the human body is described. In this example, randomized forests as in machine learning are used in which a distance difference between a target pixel and a surrounding pixel is used as a feature amount. According to the randomized forests, a plurality of decision trees are used, and the feature amount of the input data (i.e., the distance image) is calculated. Then, according to the calculation results, the decision tree are branched to obtain a final result. In the example, the feature amount is calculated on a pixel basis of the distance image, and the pixels are finally classified to belong to the particular body portion (label) by branching the decision tree based on the calculated feature amount.

The feature amount (I, x) is a difference between the target point (pixel) and the offset point nearby in the distance image, and is expressed by a formula (1).

$$f(I,x)=d_I(x)-d_I(x+\Delta)$$ formula (1)

Here, I is the distance image, x is a coordinate of the target point, $d_I(x)$ is a distance of the target point, and $d_I(x+\Delta)$ is a distance of the offset point. The offset $\Delta$ is given as follows.

$$\Delta = \frac{v}{d_I(x)}$$ formula (2)

Here, v is a offset (before the normalization) from the target point. It is noted that a predetermined position is used as the position of the offset point at the time of learning, and is normalized with the distance to accommodate a change in positional relationship between the distance image sensor 21 and the test subject S. Specifically, the distance image is enlarged as the test subject S comes closer, and thus the offset $\Delta$ is normalized with the distance of the target point.

FIG. 5 is an image diagram of target points and offset points in the distance image. In FIG. 5, a mark "+" represents the target point, a mark "x" represents the offset point, and an arrow conceptually represents the offset $\Delta$. In FIG. 5, for example, if the target point is the pixel of the head and the offset point is the background, the distance between the target point and the offset point becomes great. On the other hand, as in the torso part, if the target point and the offset point are in the upper-body, the distance between the target point and the offset point becomes small.

FIG. 6 is a diagram explaining a way of recognizing body portions using a decision tree on a pixel basis. In FIG. 6, the decision trees "tree 1" through "tree T" are illustrated. The body portion recognition part 1101 inputs the pixel of the distance image in a classifier (a plurality of decision trees), which is subject to the learning in advance, to recognize the body portion on a pixel basis. The body portion recognition part 1101 calculates, at node Nk of the decision tree, the feature amount f (I, x;Δk) of the pixel and compares the calculated feature amount with a threshold θk. The offsets Δk and the thresholds θk, with which the corresponding portions can be recognized correctly with the best score at the time of learning, are selected to be used in the calculation at the nodes. The body portion recognition part 1101 goes to the next node in a direction according to the comparison result at the nodes to reach the terminal node. At the terminal node of the decision tree, a probability distribution about the probability of which body portion the pixel belongs is obtained. In FIG. 6, $P_1$ (C) schematically illustrates the probability distribution in the decision tree "tree 1", and $P_T$ (C) schematically illustrates the probability distribution in the decision tree "tree T". c represents the body portions (labels). Then, the average probability distribution over all the trees is calculated, and the portion whose probability is the highest is the estimation result.

FIG. 7 is a diagram illustrating an overview of machine learning. A large amount of sets of the distance images of various poses and the corresponding labeled image (labeled data) is used in the machine learning. In the machine learning, the offsets Δk and the thresholds θk are determined (learned) such that the classification can be successfully performed.

Here, as an example, the randomized forests are used in the machine learning in which the difference between the distance values of the target pixel and the surrounding pixel is used as the feature amount; however, other ways may be used. For example, a Multi-class Classification method of the pixels using the distance image as an input may be performed. Further, even with respect to the randomized forests, the feature amount other than the distance value difference may be used, or a Deep Learning method in which parameter corresponding to the feature amount may be included for the learning.

Further, the body portion recognition part 1101 may recognize the terminal portion of the arms or feet with an outline detection of the human body in the distance image without using the machine learning result. This is because, with respect to the terminal portion of the arms or feet, the probability that the recognition result with the increased accuracy can be obtained with the outline detection is high even without using the machine learning result.

Figure 8:
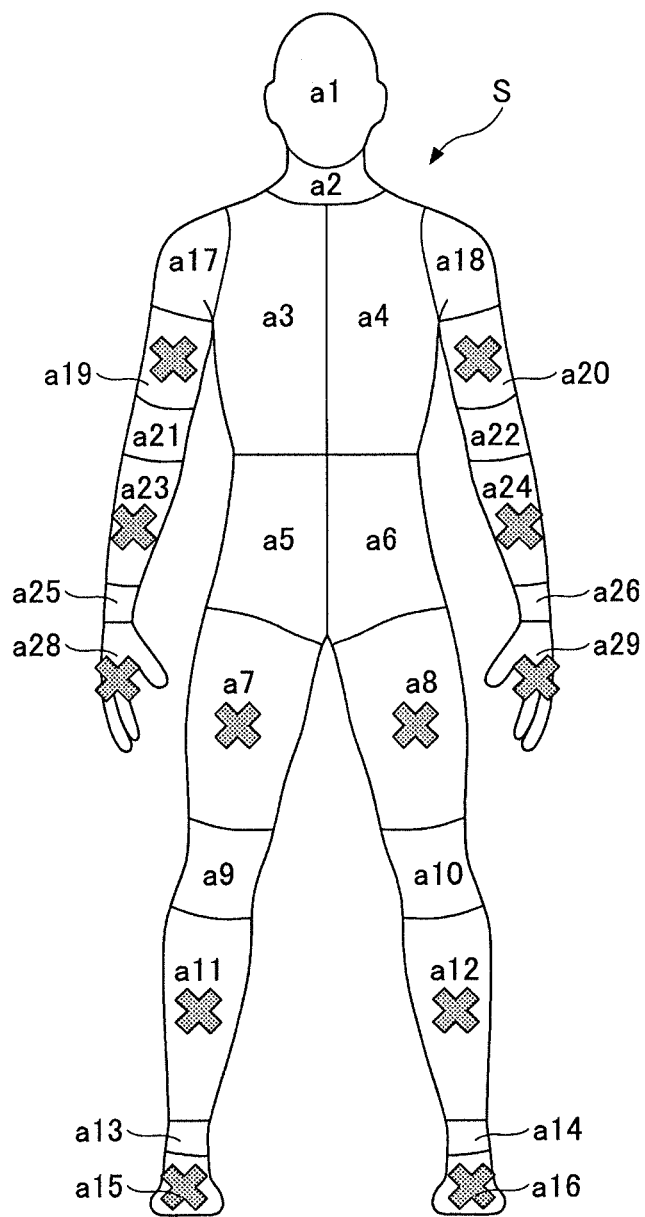
FIG. 8 is a conceptual diagram illustrating center of gravity of non-joint portions.

The non-joint portion calculation part 1102 calculate the centers of gravity of non-joint portions (an example of first and second portions) recognized by the body portion recognition part 1101 and the terminal positions. The non-joint portion calculation part 1102 calculates the centers of gravity of non-joint portions a7, a8, a11, a12, a19, a20, a23, a24, and the terminal positions a15, a16, a28, a29, as indicated by "x" marks in FIG. 8.

Figure 9:
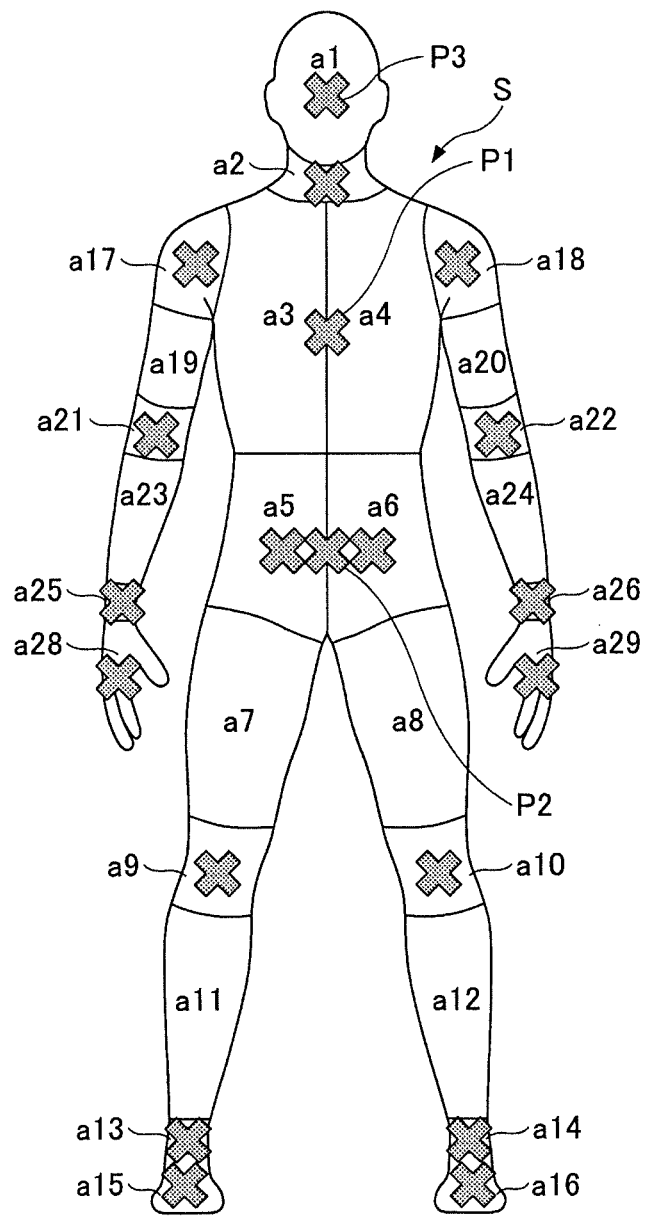
FIG. 9 is a conceptual diagram illustrating center of gravity of joint portions, etc.
Figure 10:
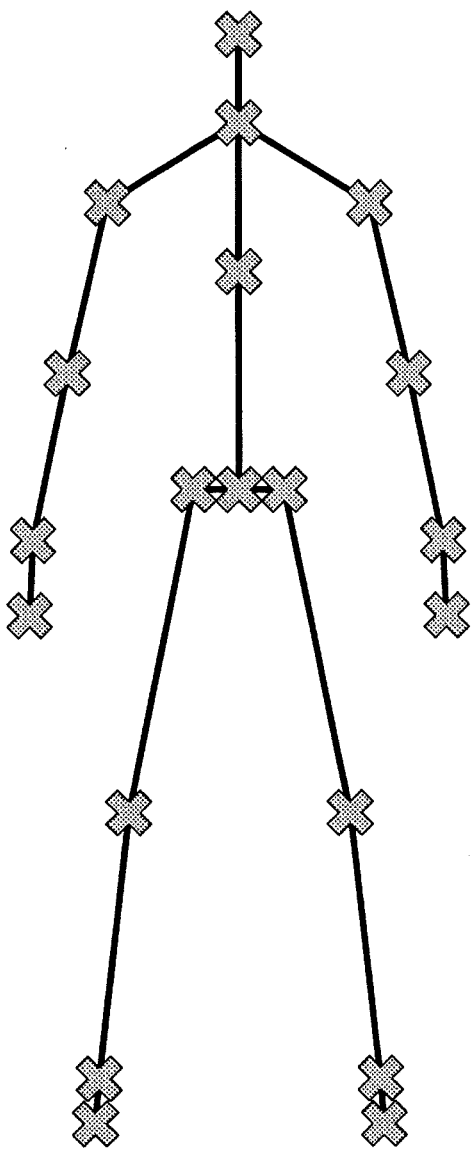
FIG. 10 is a conceptual diagram illustrating a recognition result of a skeleton.

The joint position calculation part 1103 calculates the center of gravity of the joint portions recognized by the body portion recognition part 1101. The joint position calculation part 1103 calculates the centers of gravity of the joint portions, and other bone reference positions P1, P2, P3, as indicated by "x" marks in FIG. 9. In this case, the joint position calculation part 1103 may further recognize the bone (skeleton) based on the centers of gravity of the joint portions and the bone reference positions P1, P2, P3, as schematically illustrated in FIG. 10.

Figure 11:
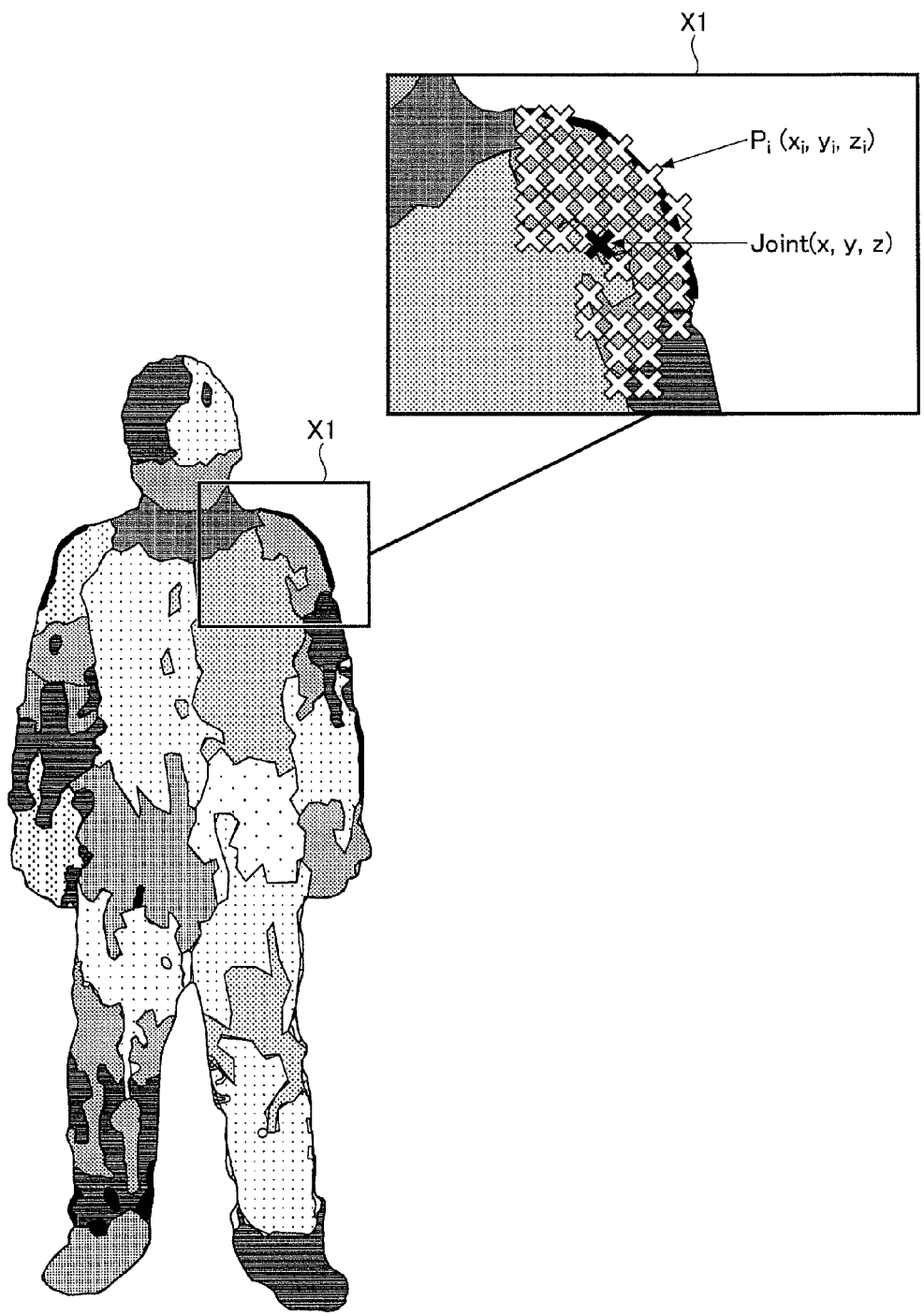
FIG. 11 is a diagram explaining an example of a way of calculating center of gravity.

FIG. 11 is a diagram explaining an example of a way of calculating the center of gravity that can be used in the non-joint portion calculation part 1102 and the joint position calculation part 1103. FIG. 11 illustrates the recognition result of the portions by the body portion recognition part 1101, and also illustrates a range X1 in an enlarged manner. Here, with reference to the enlarged illustration of the range X1, a way of calculating the center of gravity of the left shoulder (i.e., the joint portion) is explained. In the enlarged illustration of the range X1, the points Pi indicated by white marks "x" represent three-dimensional coordinates of the pixels that are classified as the "shoulder". In this case, the center of gravity Joint (x, y, z) indicated by a black mark "x" may be determined by averaging the three-dimensional coordinates of all the points Pi, as given by a formula 3.

$$\text{Joint} = \frac{1}{n}\sum_{i=0}^{n} P_i \quad \text{formula (3)}$$

It is noted that in formula 3 "n" is the number of the points Pi.

The measurement item determination part 112 determines the measurement item according to an input (from the user) related to the measurement item via the input part 107. FIG. 12 is a table illustrating an example of the measurement items. In FIG. 12, "No." represents the number of the measurement item, "portion name" represents inspection portions related to the ROM of the measurement target, and "motion direction" represents the motion direction of the measurement target (in which the ROI is measured). Further, in FIG. 12, "particular measurement item" represents whether the measurement item is a particular measurement item (see FIG. 14B) for which a particular joint angle calculation process can be used. In FIG. 12, a "circle mark" indicates that the measurement item is the particular measurement item, and a mark "x" indicates that the measurement item is not the particular measurement item.

Figure 13A:
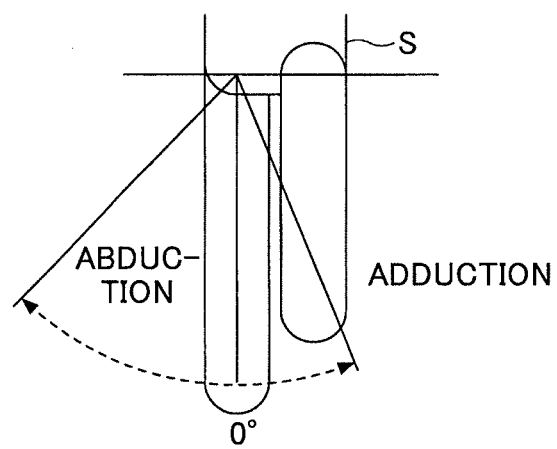
FIG. 13A is a diagram explaining measurement items related to hip joints.
Figure 13B:
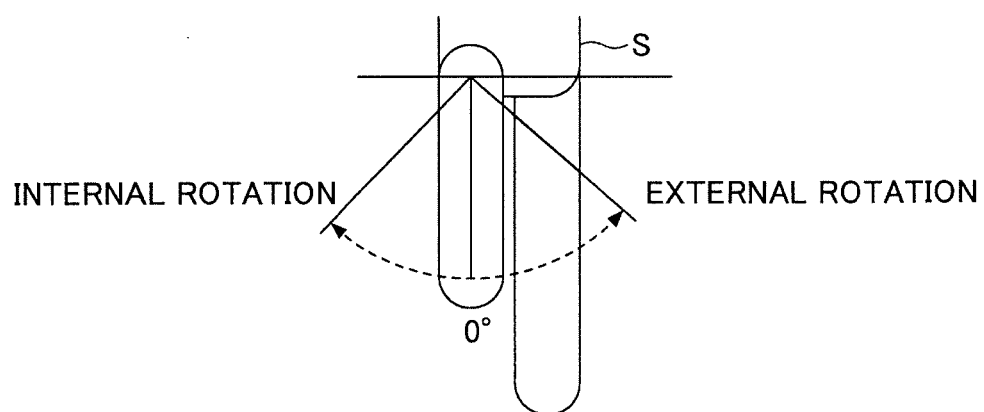
FIG. 13B is a diagram explaining measurement items related to hip joints.

For example, the measurement item related to the hip includes an abduction/adduction of the hip joint (No. 20) and an external rotation/internal rotation of the hip joint (No. 21). FIG. 13A and FIG. 13B are diagrams explaining measurement items related to hip joints. FIG. 13A is a diagram explaining the abduction/adduction of the hip joint, and FIG. 13B is a diagram explaining the external rotation/internal rotation of the hip joint. It is noted that, in FIG. 13A and FIG. 13B, only the lower-body of the test subject S on its back is schematically illustrated in a top view. Here, the abduction/adduction and the external rotation/internal rotation of the right hip joint are explained; however, the abduction/adduction and the external rotation/internal rotation of the left hip joint are substantially the same. In the case of the measurement item being the abduction/adduction of the right hip joint, the test subject S moves the right foot in the extended state in the left-and-right direction, as illustrated in FIG. 13A. In the case of the measurement item being the abduction/adduction of the right hip joint, the joint angles in such a motion are calculated. In the case of the measurement item being the external rotation/internal rotation of the right hip joint, the test subject S moves the distal portion from the right knee in the left-and-right direction while keeping the fixed right knee angle, as illustrated in FIG. 13B. In the case of the measurement item being the external rotation/internal rotation of the right hip joint, the joint angles in such a motion are calculated. It is noted that, in the case of the measurement item being the abduction/adduction or the external rotation/internal rotation of the right hip joint, an angle between a direction in which the foot in motion extends and a basic axis, for example, is to be calculated as the joint angle, as illustrated in FIG. 13A and FIG. 13B. In the case of the abduction/adduction, the basic axis is a line perpendicular to a line connecting anterior superior iliac spines on opposite sides. It is noted that the basic axes together with the measurement items as illustrated in FIG. 12 are described in "DISPLAY AND MEASUREMENT METHOD OF ROM OF JOINT" by Japanese Orthopaedic Association and Japan Association of Rehabilitation Medicine.

When the measurement item determination part 112 determines the measurement item, the measurement item determination part 112 reports the determined measurement item to the joint angle calculation part 120, the ROM calculation part 136, and the output part 138.

The ordinary joint angle calculation part 121 calculates the joint angle of the joint predetermined according to the measurement item (in the case of the measurement item being other than the particular measurement item) reported by the measurement item determination part 112. Specifically, at first, the ordinary joint angle calculation part 121 obtains the centers of gravity (simply referred to as "a joint coordinate", hereinafter) of the joint portions from the joint position calculation part 1103. It is noted that the ordinary joint angle calculation part 121 may obtain necessary joint coordinates (the joint coordinates related to the joint portion predetermined according to the measurement item reported by the measurement item determination part 112) only. The ordinary joint angle calculation part 121 calculates the joint angle based on the obtained joint coordinates. For example, the ordinary joint angle calculation part 121 can calculate, based on the angle between the line (an example of a second line) connecting two or more joint coordinates predetermined on a measurement item basis and the basic axis predetermined on a measurement item basis, the joint angle of the test subject S. The joint angle calculation process by the ordinary joint angle calculation part 121 is referred to as an "ordinary joint angle calculation process".

The particular joint angle calculation part 122 calculates the joint angle of the joint predetermined according to the measurement item (in the case of the measurement item being the particular measurement item) reported by the measurement item determination part 112. Specifically, at first, the particular joint angle calculation part 122 obtains the centers of gravity (simply referred to as "a non-joint coordinate", hereinafter) of the non-joint portions and the terminal portions from the non-joint portion calculation part 1102. It is noted that the particular joint angle calculation part 122 may obtain necessary non-joint coordinates (the non-joint coordinates related to the non-joint portion or the terminal portion predetermined according to the measurement item reported by the measurement item determination part 112) only. The particular joint angle calculation part 122 calculates the joint angle based on the obtained non-joint coordinates. For example, the particular joint angle calculation part 122 can calculate, based on the angle between the line (an example of a first line) connecting two or more non-joint coordinates predetermined on a measurement item basis and the basic axis predetermined on a measurement item basis, the joint angle of the test subject S. The joint angle calculation process by the particular joint angle calculation part 122 is referred to as a "particular joint angle calculation process". The concrete examples of the particular joint angle calculation process are described hereinafter.

The ROM calculation part 136 calculates the ROM of the joint based on the joint angle data (in the motion corresponding to the measurement item) calculated by the ordinary joint angle calculation part 121 or the particular joint angle calculation part 122. The ROM calculation part 136 may calculate the ROM of the joint in a range that is predetermined on a measurement item basis and meets a condition related to the ROM of the joint. The condition related to the ROM of the joint may be such that the joint moves in a particular plane, such as a sagittal plane, coronal plane, etc. For example, the ROM calculation part 136 may regard the maximum of the joint angles calculated with respect to the measurement item as the ROM of the joint related to the measurement item.

The output part 138 outputs information representing the ROM of the joint calculated by the ROM calculation part 136 on a display part (not illustrated). For example, the output part 138 outputs numeral values representing the ROM of the joint together with the corresponding measurement item. It is noted that the display part is implemented by a display such as a CRT (Cathode-Ray Tube) display, a liquid crystal display, etc.

Figure 14A:
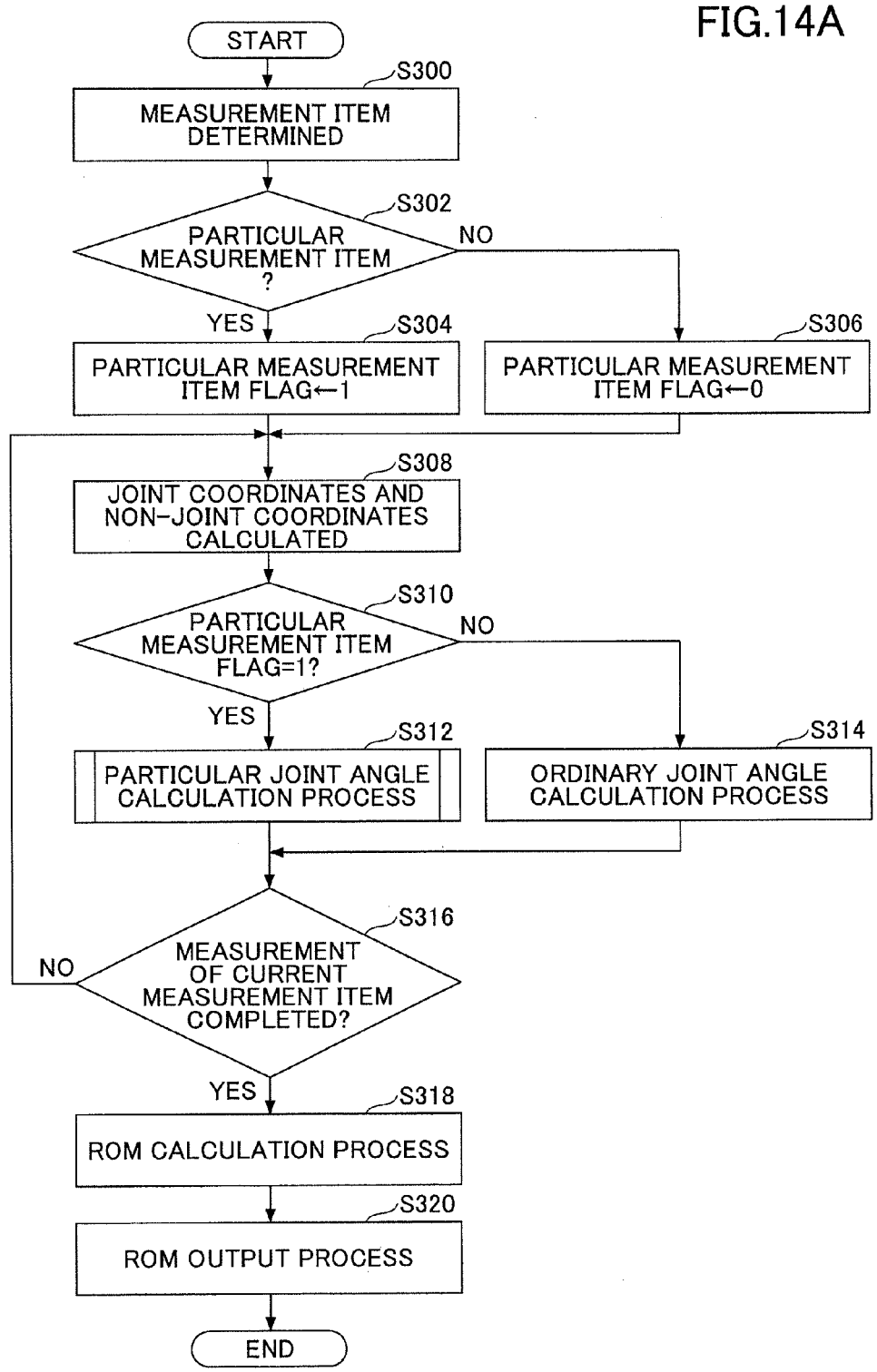
FIG. 14A is a flowchart illustrating an example of a process by a processing device.

FIG. 14A is a flowchart illustrating an example of a process by a processing device 100. The process illustrated in FIG. 14A may be initiated when a measurement start instruction is input via the input part 107, for example. Alternatively, the process illustrated in FIG. 14A is initiated when the distance image from the distance image sensor 21 is input to the processing device 100, for example. It is noted that the distance image from the distance image sensor 21 may be input at a predetermined cycle (frame cycle).

In step S300, the measurement item determination part 112 determines the measurement item according to an input (from the user) related to the measurement item via the input part 107.

In step S302, the measurement item determination part 112 determines whether the measurement item determined in step S300 is the particular measurement item (see FIG. 12). If the determination result is "YES", the process illustrated in FIG. 14A goes to step S304, otherwise the process illustrated in FIG. 14A goes to step S306.

In step S304, the measurement item determination part 112 sets a particular measurement item flag to "1".

In step S306, the measurement item determination part 112 sets the particular measurement item flag to "0".

In step S308, the body portion recognition part 1101 recognizes the portions of the human body of the test subject S in the distance image to derive the non-joint coordinates and the joint coordinates. It is noted that the body portion recognition part 1101 may derive only non-joint coordinates or the joint coordinates according to the particular measurement item flag. For example, when the particular measurement item flag is "1", the non-joint portion calculation part 1102 operates to calculate the non-joint coordinates. On the other hand, when the particular measurement item flag is "0", the joint position calculation part 1103 operates to calculate the joint coordinates.

In step S310, the joint angle calculation part 120 determines whether the particular measurement item flag is "1". If the determination result is "YES", the process illustrated in FIG. 14A goes to step S312, otherwise the process illustrated in FIG. 14A goes to step S314.

In step S312, the particular joint angle calculation part 122 performs the particular joint angle calculation process. The particular joint angle calculation process is as described above. An example of the particular joint angle calculation process is described hereinafter with reference to FIG. 14B.

In step S314, the ordinary joint angle calculation part 121 performs the ordinary joint angle calculation process. The ordinary joint angle calculation process is as described above.

In step S316, the body portion recognition part 1101 determines whether the measurement related to the current measurement item has completed. The measurement related to the measurement item ends when a measurement end instruction is input via the input part 107, for example. In this case, whether the measurement related to the current measurement item has completed can be determined based on the measurement end instruction. Alternatively, the measurement may be ended when the input of the distance image from the distance image sensor 21 ends. Alternatively, the measurement may be ended automatically based on the calculation result of the joint angle by the joint angle calculation part 120. If the determination result is "YES", the process illustrated in FIG. 14A goes to step S318, otherwise the process illustrated in FIG. 14A returns to step S308 to continue the processes with respect to the next frame.

In step S318, the ROM calculation part 136 calculates the ROM of the joint based on the joint angle data (the joint angles obtained during the current measurement session) obtained in step S312 and step S314.

In step S3120, the output part 138 outputs the information representing the ROM of the joint calculated by the ROM calculation part 136 on a display part (not illustrated).

Figure 15:
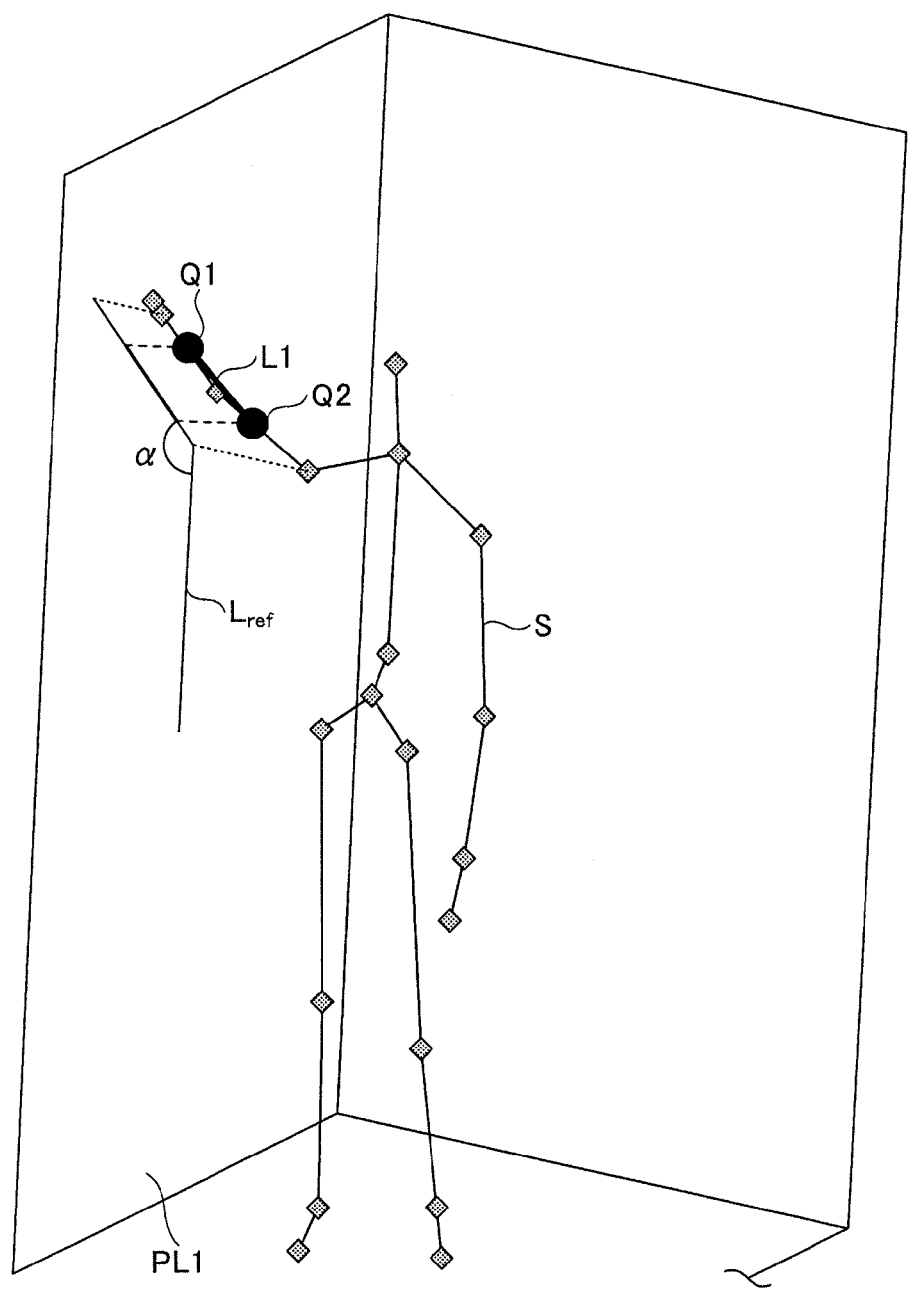
FIG. 15 is a diagram explaining a process illustrated in FIG. 14.

FIG. 14B is a flowchart illustrating an example of a joint angle calculation way by the particular joint angle calculation part 122. The process illustrated in FIG. 14B corresponds to the particular joint angle calculation process illustrated in FIG. 14A. FIG. 15 is a diagram explaining the process illustrated in FIG. 14B. In FIG. 15, an example in the case where the measurement item is the flexion of the shoulder joint (see No. 3 in FIG. 12) is illustrated. In FIG. 15, the skeleton of the test subject S is schematically illustrated. It is noted that, in the case where the measurement item is the flexion of the shoulder joint, the test subject S moves the arm from a right under position upwardly with the arm being extended, as illustrated in FIG. 15.

In step S400, the particular joint angle calculation part 122 obtains the non-joint coordinates. It is noted that the particular joint angle calculation part 122 may obtain only two non-joint coordinates predetermined on a measurement basis.

In step S401, the particular joint angle calculation part 122 calculates (generates) a vector (line) connecting two non-non-joint coordinates predetermined on a measurement basis. In the example illustrated in FIG. 15, the vector L1 connecting the non-joint coordinates (i.e., between the points Q1 and Q2) of the brachium and the forearm of the test subject S. It is noted that the brachium and the forearm are the non-joint portions.

In step S402, the particular joint angle calculation part 122 projects the generated vector on a reference plane. For example, in the case where the measurement item is the flexion of the shoulder joint, as illustrated in FIG. 15, the reference plane is a plane (i.e., the sagittal plane) PL1 perpendicular to the human body, and thus the vector L1 is projected on the plane PL1.

In step S404, the particular joint angle calculation part 122 calculates the angle between the basic axis on the reference plane and the projected vector. In the case where the measurement item is the flexion of the shoulder joint, as illustrated in FIG. 15, the vertical plane on the sagittal plane is the basic axis, and the angle α between the vector L1 (projected on the plane PL1) calculated in step S402 and the basic axis $L_{ref}$ is calculated. The angle α is the flexion angle (an example of the joint angle) of the shoulder joint.

In step S406, the particular joint angle calculation part 122 outputs the flexion angle determined in step S404. For example, the particular joint angle calculation part 122 may store the flexion angles calculated during the current measurement session in a predetermined storage area.

It is noted that, in the example illustrated in FIG. 14B, the vector L1 connecting the non-joint coordinates is generated and then the vector L1 is projected on the plane PL1; however, as an equivalent variant, the non-joint coordinates may be projected on the plane PL1 and then a vector connecting the projected non-joint coordinates may be generated. In both cases, resultant vectors on the plane PL1 are the same.

Here, according to an comparative example in which the flexion angle of the shoulder joint is calculated by the ordinary joint angle calculation process, a vector connecting the joint coordinates of the shoulder and the carpus, which are the joint portions, is generated, and the generated vector is projected on the plane PL1. Then, the ordinary joint angle calculation part 121 calculates, as the flexion angle, an angle between the projected vector and the basic axis.

Figure 16:
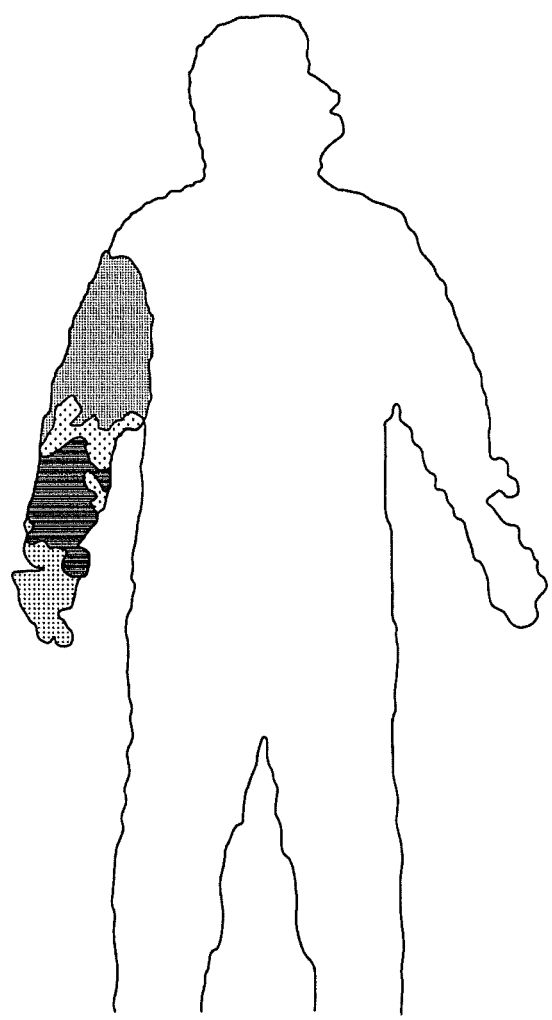
FIG. 16 is a diagram illustrating an example of a recognition result of body portions of a part of a test subject.

According to the way of recognizing the portions of the test subject S based on the distance image as described above, the recognition result is obtained by statistically estimating the label (portion) into which respective pixels are classified based on the learned data. For this reason, portion and another portion may not be divided with a clear boundary therebetween, and thus the boundary becomes vague such that a plurality of portions are mixed, as illustrated in FIG. 16. FIG. 16 is a diagram illustrating an example of the recognition result of the portions, that is to say, the right brachium, the right elbow, the right forearm, the right carpus, and the right hand (the terminal portion) of the test subject S by the body portion recognition part 1101. In the example illustrated in FIG. 16, the boundary with respect to the joint portions with a relatively small area, such as the carpus and the elbow becomes vague. With respect to the joint portions with a relatively small area, such as the carpus and the elbow, when the boundary becomes vague, the accuracy of the calculated joint position (center of gravity) tends to be worse. This is because even a slight error in the boundary substantially affects the accuracy of the center of gravity due to the relatively small area. If the accuracy of the calculated joint position becomes worse, it becomes difficult to accurately calculate the joint angle with the ordinary joint angle calculation process.

On the other hand, the joint portions such as the shoulder, the elbow, the carpus, the knee, and the ankle are small in area, but the non-joint portions such as the brachium, the forearm, the thigh, the anticnemion, etc., are relatively great in area. Thus, in the case of the non-joint portions such as the brachium, the forearm, the thigh, the anticnemion, etc., which are relatively great in area, the probability that the center of gravity can be accurately calculated from the center of gravity becomes high even when the boundary becomes vague.

Here, for example, there are some measurement items, among the measurement items in "DISPLAY AND MEASUREMENT METHOD OF ROM OF JOINT" illustrated in FIG. 12, for which the measurement can be performed using the non-joint portions even without the joint positions. For example, with respect to the measurement item (i.e., the particular measurement item) for which the field of "particular measurement item" is given a circle mark in FIG. 12, the joint angles and thus the ROM based on the joint angles can be calculated using the recognition result (non-joint coordinates) of the non-joint portions.

In order to effectively utilize these characteristics, according to the embodiment, with respect to the joint angle related to the particular measurement item, instead of the ordinary joint angle calculation process by the ordinary joint angle calculation part 121, the particular joint angle calculation process by the particular joint angle calculation part 122 is performed. The particular joint angle calculation part 122 calculates the joint angle using the coordinates (i.e., the non-joint coordinates) of the non-joint portions with the relatively great area without using the coordinates (i.e., the joint coordinates) of the joint portions with the relatively small area. Thus, according to the embodiment, it becomes possible to increase the accuracy of the calculated joint angle related to the particular measurement item.

Further, with respect to the joint portions with the relatively small area such as the elbow, the carpus, etc., the recognition accuracy is not good, and thus the variation in the calculated center of gravity between frames tends to become greater. For example, the accuracy of the calculated joint position is unstable from one frame to another, such that the accuracy of the calculated joint positions is high with respect to a certain frame while the accuracy of the calculated joint positions is low with respect to another frame.

In contrast, according to the embodiment, with respect to the ROM of the joint related to the particular measurement item, the ROM of the joint is calculated based on the joint angles calculated by the particular joint angle calculation part 122 instead of the ordinary joint angle calculation part 121. The particular joint angle calculation part 122 calculates the joint angle using the coordinates (i.e., the non-joint coordinates) of the non-joint portions with the relatively great area without using the coordinates (i.e., the joint coordinates) of the joint portions with the relatively small area, as described above. Thus, the particular joint angle calculation part 122 can calculate the joint angle with the stably increased accuracy during the motion of the test subject S corresponding to the measurement item.

Next, with reference to FIG. 17 through FIG. 29, concrete examples of the way of calculating the joint angle (i.e., the particular joint angle calculation process), with respect to some of the particular measurement items in "DISPLAY AND MEASUREMENT METHOD OF ROM OF JOINT" as illustrated in FIG. 12 are explained. Here, as an comparative example, the concrete examples of the ordinary joint angle calculation process related to the corresponding measurement item by the ordinary joint angle calculation part 121 are explained in contrast. In the following, for the sake of the explanation, the example in which the particular joint angle calculation process is used is referred to as an "embodiment", and the example in which the ordinary joint angle calculation process is used is referred to as a "comparative example".

Figure 17:
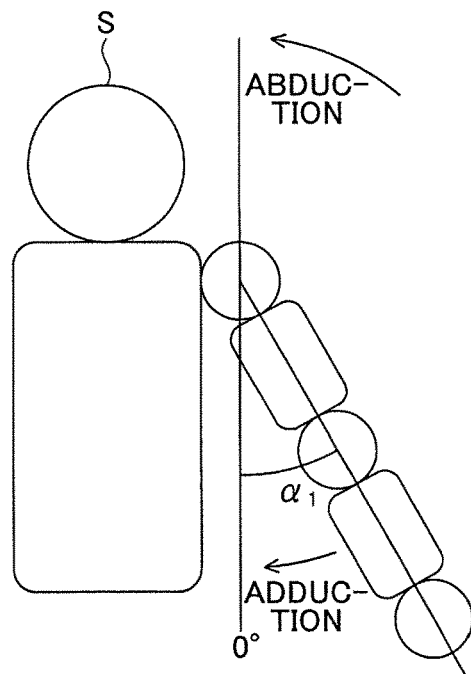
FIG. 17 is a diagram explaining abduction/adduction of a shoulder joint.

FIG. 17 is a diagram explaining the abduction/adduction of the shoulder joint. In FIG. 17, a relevant part of the test subject S is schematically illustrated in a front view. In the case of the measurement item being the abduction/adduction of the shoulder joint, the test subject S is in a standing or seating state and moves the arm in the extended state in the up-and-down direction, as illustrated in FIG. 17. In the case of the measurement item being the abduction/adduction of the shoulder joint, the joint angles $\alpha 1$ in such a motion are calculated. The joint angles $\alpha 1$ are between the vertical line (basic axis: the vertical line to the floor through the acromion) from the shoulder and the arm.

Figure 18A:
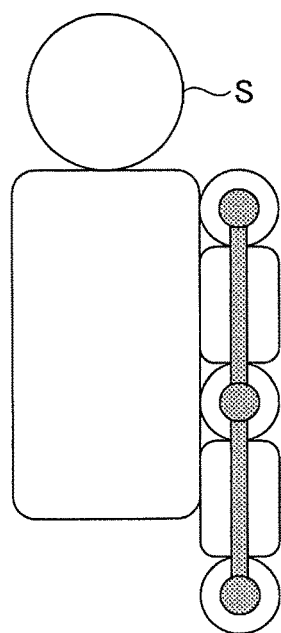
FIG. 18A is a diagram explaining a comparative example.
Figure 18B:
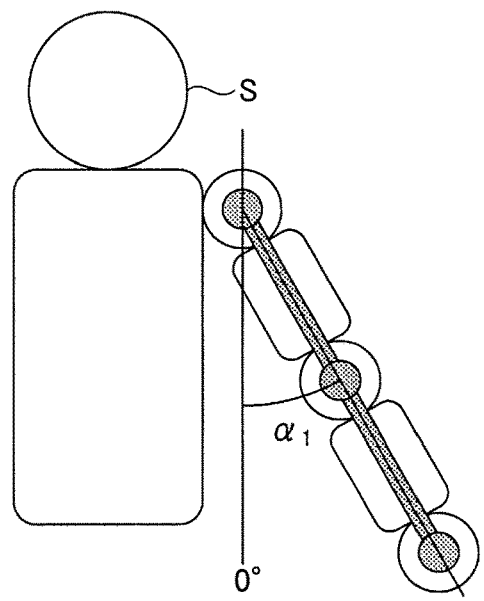
FIG. 18B is a diagram explaining a comparative example.
Figure 19A:
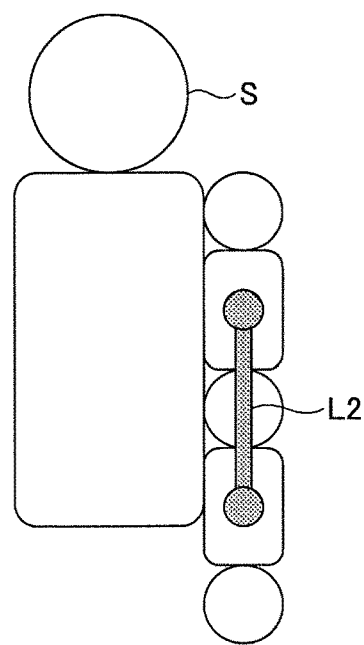
FIG. 19A is a front view of the test subject in an initial pose related to the abduction/adduction of the shoulder joint.
Figure 19B:
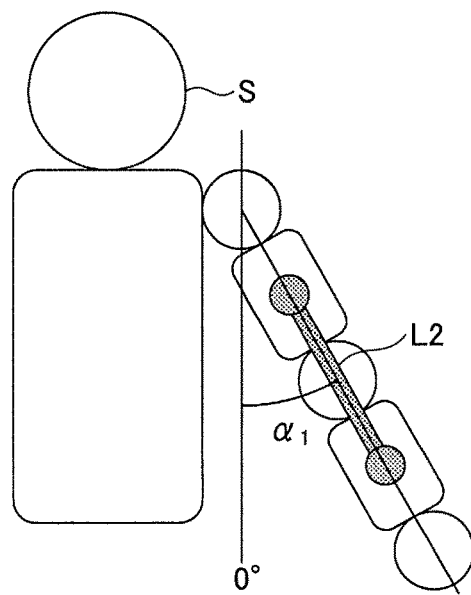
FIG. 19B is a front view of the test subject in a pose related to the abduction/adduction of the shoulder joint during a measurement session.

FIG. 18A and FIG. 18B are diagrams explaining the comparative example. FIG. 18A is a front view of the test subject S in the initial pose, and FIG. 18B is a front view of the test subject S in the pose during the measurement session. FIG. 19A and FIG. 19B are diagrams explaining the embodiment. FIG. 19A is a front view of the test subject S in the initial pose, and FIG. 19B is a front view of the test subject S in the pose during the measurement session.

According to the comparative example, as illustrated in FIG. 18A and FIG. 18B, a line (i.e., a vector) is determined based on at least two centers of gravity of the shoulder, the elbow, and the carpus, and the joint angles α1 are calculated based on the determined line. In contrast, according to the embodiment, as illustrated in FIG. 19A and FIG. 19B, a line, which is geometrically equivalent to the line according to the comparative example, is determined based on the centers of gravity of the non-joint portions, that is to say, the brachium and the forearm, and the joint angles α1 are calculated based on the determined line. For example, the line L2 connecting the centers of gravity of the non-joint portions, that is to say, the brachium and the forearm, is projected on the coronal plane, and the angle between the projected line on the coronal plane and the basic axis is calculated. Thus, according to the embodiment, as described above, it becomes possible to increase the accuracy of the calculated joint angle related to the abduction/adduction of the shoulder joint, with respect to the comparative example. As a result of this, according to the embodiment, it becomes possible to increase the accuracy of the calculated ROM of the joint related to the abduction/adduction of the shoulder joint.

Figure 20:
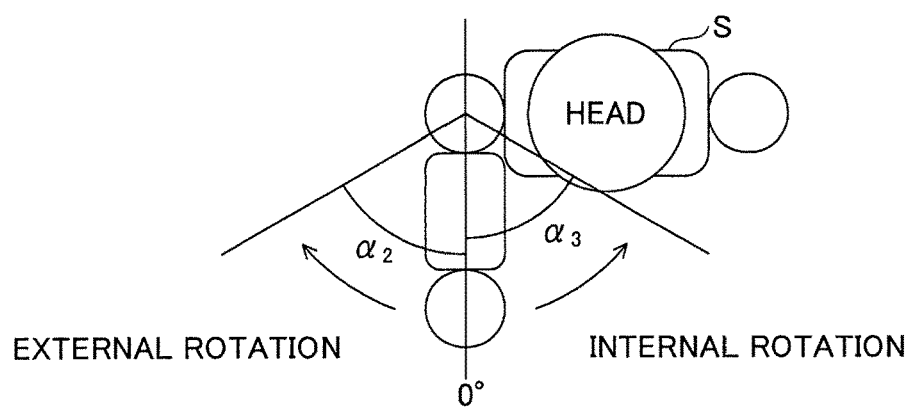
FIG. 20 is a diagram explaining external rotation/internal rotation of the shoulder joint.

FIG. 20 is a diagram explaining the external rotation/internal rotation of the shoulder joint. In FIG. 20, a relevant part of the test subject S is schematically illustrated in a top view. In the case of the measurement item being the external rotation/internal rotation of the shoulder joint, the test subject S is in a standing or seating state and moves the arm bended at right angle in the left-and-right direction from the initial front position, as illustrated in FIG. 20. In the case of the measurement item being the external rotation/internal rotation of the shoulder joint, the joint angles α2 and α3 in such a motion are calculated. The joint angles α2 and α3 are between the basic axis (i.e., the vertical line to the coronal plane through the elbow) and the forearm.

Figure 21:
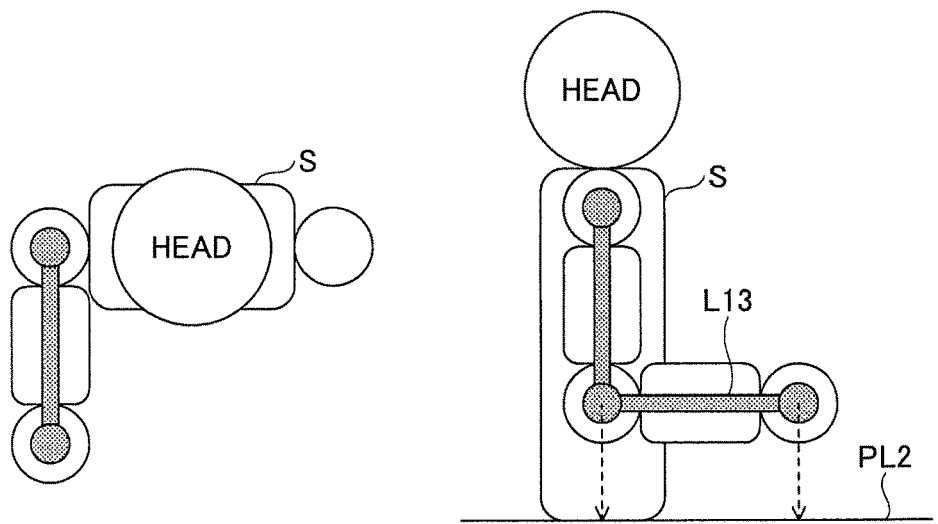
FIG. 21 is a diagram explaining respective dimensions.
Figure 22:
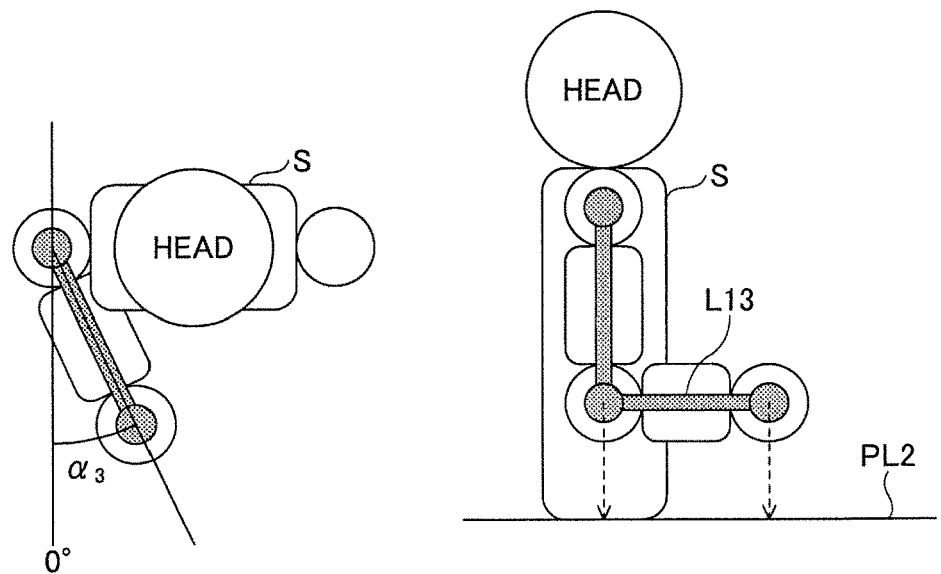
FIG. 22 is a diagram explaining respective dimensions.
Figure 23:
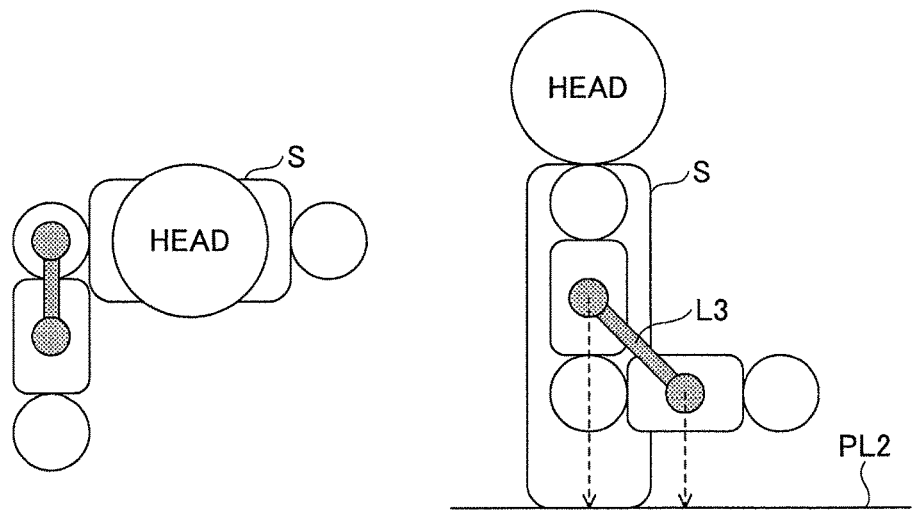
FIG. 23 illustrates front and side views of the test subject in an initial pose related to the external rotation/internal rotation of the shoulder joint.
Figure 24:
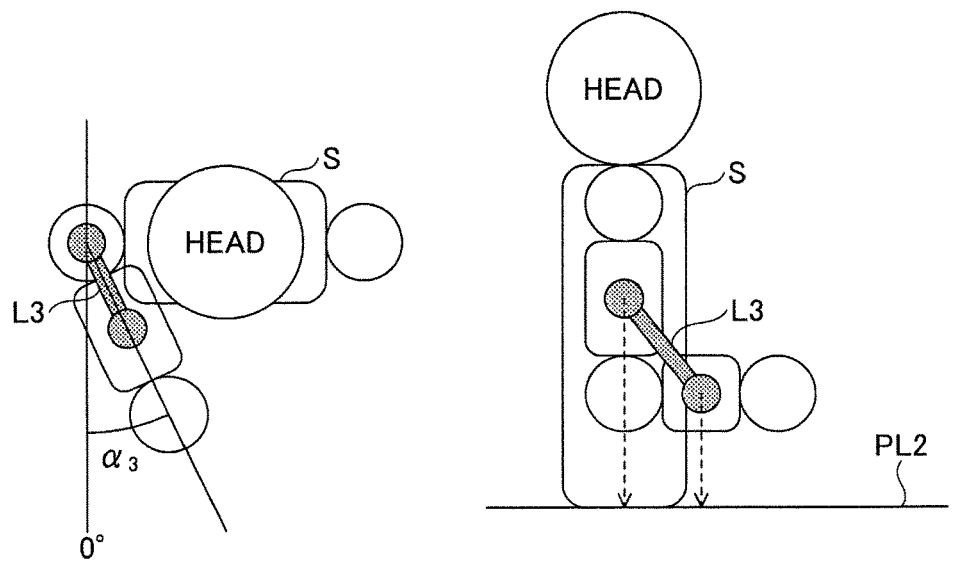
FIG. 24 illustrates top and side views of the test subject in a pose related to the external rotation/internal rotation of the shoulder joint during a measurement session.

FIG. 21 and FIG. 22 are diagrams explaining the comparative example. FIG. 21 illustrates top and side views of the test subject S in the initial pose, and FIG. 22 illustrates top and side views of the test subject S in the pose during the measurement session. FIG. 23 and FIG. 24 are diagrams explaining the embodiment. FIG. 23 illustrates top and side views of the test subject S in the initial pose, and FIG. 24 illustrates top and side views of the test subject S in the pose during the measurement session. It is noted that, in FIG. 21 through FIG. 24, downward arrows (dotted line) in the side view on the right conceptually represents the "projection" of the corresponding lines.

According to the comparative example, as illustrated in FIG. 21 and FIG. 22, a line L13 connecting the centers of gravity (two centers of gravity) of the two joint portions, that is to say, the elbow and the carpus is projected on a horizontal plane PL2, and the angle (the joint angle α3 in FIG. 22) between the projected line L13 on the horizontal plane PL2 and the basic axis is calculated. In contrast, according to the embodiment, as illustrated in FIG. 23 and FIG. 24, a line L3 connecting the centers of gravity of the two non-joint portions, that is to say, the brachium and the forearm is projected on a horizontal plane PL2, and the angle between the projected line on the horizontal plane PL2 and the basic axis is calculated. Here, as is clear from contrast between the side views of FIG. 21 and FIG. 23, the line L13 to be projected according to the comparative example spatially passes through the elbow, while the line L3 according to the embodiment does not spatially pass through the elbow. However, in the case of the external rotation/internal rotation of the shoulder joint, actual measurement involves the projection on the horizontal plane PL2, and thus only the angle in the top view may suffice. Therefore, the line L3 can be used to calculate the joint angle related to the external rotation/internal rotation of the shoulder joint. Thus, according to the embodiment, as described above, it becomes possible to increase the accuracy of the calculated joint angle related to the external rotation/internal rotation of the shoulder joint, with respect to the comparative example. As a result of this, according to the embodiment, it becomes possible to increase the accuracy of the calculated ROM of the joint related to the external rotation/internal rotation of the shoulder joint.

It is noted that, in the example illustrated in FIG. 23 and FIG. 24, the line L3 connecting the centers of gravity of the two non-joint portions, that is to say, the brachium and the forearm, is used; however, the terminal portion of the arm (an example of the first portion and the second portion) determined from the edge detection may be used, instead of the forearm.

Further, in the example illustrated in FIG. 23 and FIG. 24, the external rotation/internal rotation of the shoulder joint is described; however, the same holds true for the horizontal flexion/horizontal extension of the shoulder joint. Specifically, in the case of the horizontal flexion/horizontal extension of the shoulder joint, the line connecting the centers of gravity of the two non-joint portions, that is to say, the brachium and the forearm, can be used to calculate the joint angles and the ROM based on the calculated joint angles.

Figure 25:
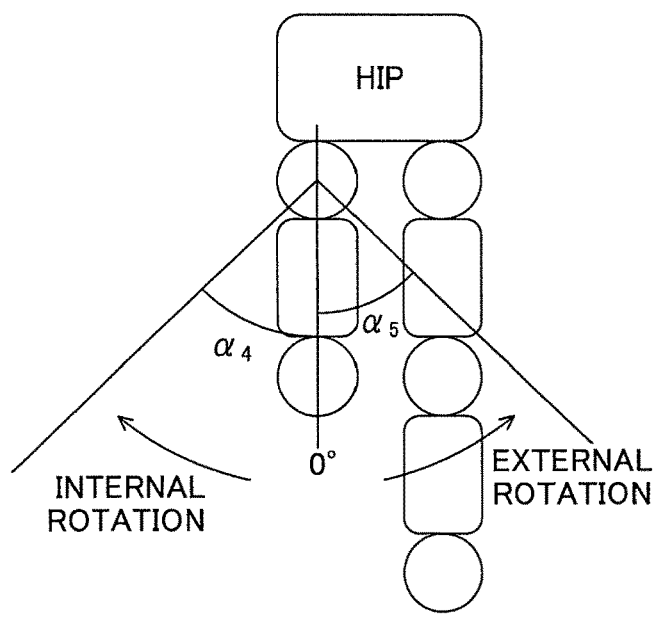
FIG. 25 is a diagram explaining external rotation/internal rotation of the hip joint.

FIG. 25 is a diagram explaining the external rotation/internal rotation of the hip joint. In FIG. 25, a relevant part of the test subject S is schematically illustrated in a top view. When the measurement item is the external rotation/internal rotation of the hip joint, as described above with reference to FIG. 13B, the test subject S is in a supine position and moves the distal portion from the knee in the left-and-right direction while bending the knee at the right angle, as illustrated in FIG. 25. In the case of the measurement item being the external rotation/internal rotation of the hip joint, the joint angles α4 and α5 in such a motion are calculated. The joint angles α4 and α5 are between the basic axis and the anticnemion (leg).

Figure 26:
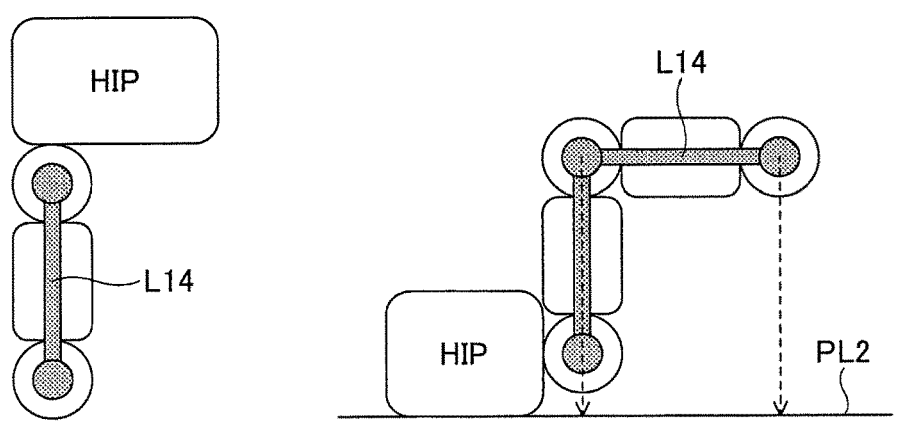
FIG. 26 is a diagram explaining respective dimensions.
Figure 27:
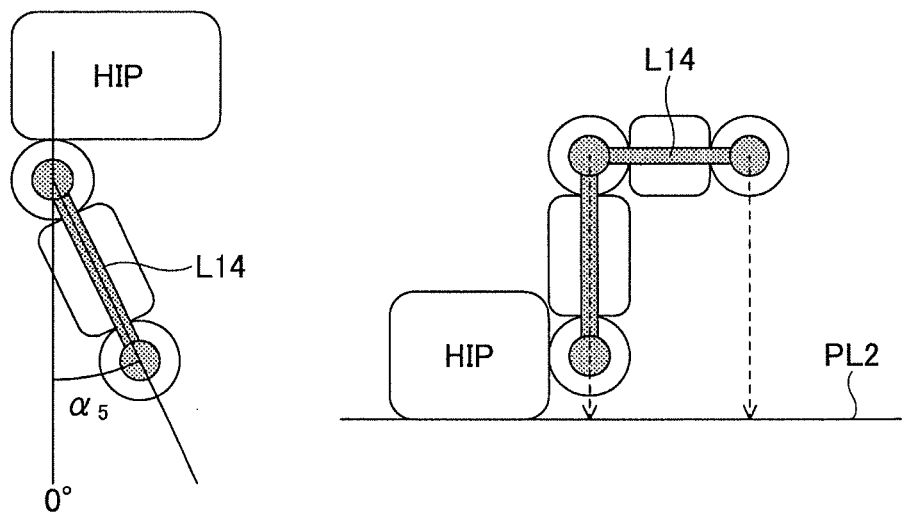
FIG. 27 is a diagram explaining respective dimensions.
Figure 28:
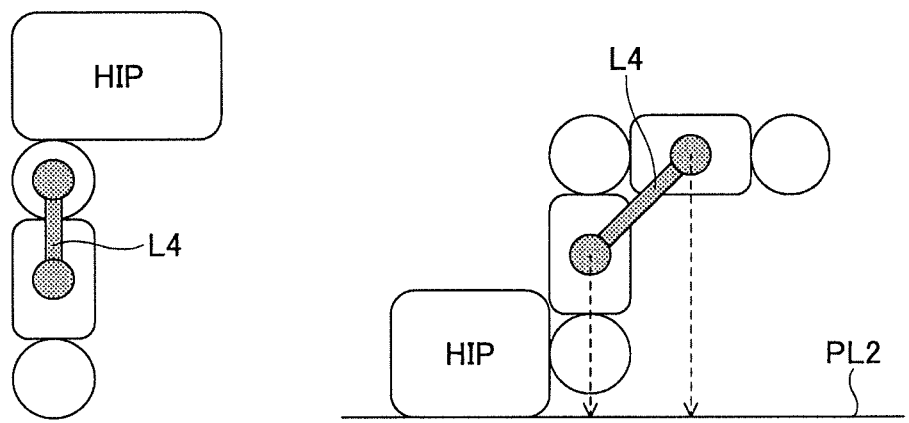
FIG. 28 illustrates front and side views of the test subject in an initial pose related to the external rotation/internal rotation of the hip joint.
Figure 29:
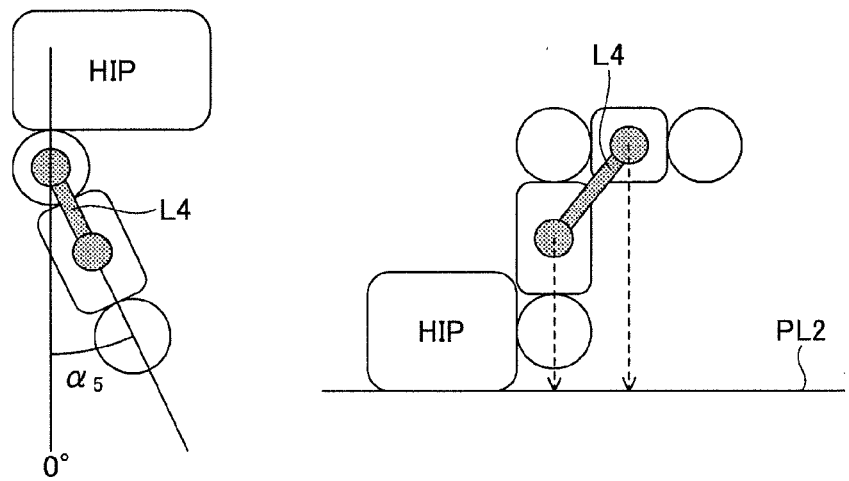
FIG. 29 illustrates top and side views of the test subject in a pose related to the external rotation/internal rotation of the hip joint during a measurement session.

FIG. 26 and FIG. 27 are diagrams explaining the comparative example. FIG. 26 illustrates top and side views of the test subject S in the initial pose, and FIG. 27 illustrates top and side views of the test subject S in the pose during the measurement session. FIG. 28 and FIG. 29 are diagrams explaining the embodiment. FIG. 28 illustrates top and side views of the test subject S in the initial pose, and FIG. 29 illustrates top and side views of the test subject S in the pose during the measurement session. It is noted that, in FIG. 26 through FIG. 29, downward arrows (dotted line) in the side view on the right conceptually represents the "projection" of the corresponding lines.

According to the comparative example, as illustrated in FIG. 26 and FIG. 27, a line L14 connecting the centers of gravity (two centers of gravity) of the two joint portions, that is to say, the knee and the ankle is projected on the horizontal plane, and the angle (the joint angle α5 in FIG. 27) between the projected line L14 on the horizontal plane and the basic axis is calculated. In contrast, according to the embodiment, as illustrated in FIG. 28 and FIG. 29, a line L4 connecting the centers of gravity of the two non-joint portions, that is to say, the thigh and the anticnemion are projected on a horizontal plane PL2, and the angle between the projected line on the horizontal plane PL2 and the basic axis is calculated. Here, as is clear from contrast between the side views of FIG. 26 and FIG. 28, the line L14 to be projected spatially passes through the knee in the comparative example, while the line L4 according to the embodiment does not spatially pass through the knee. However, in the case of the external rotation/internal rotation of the hip joint, actual measurement involves the projection on the horizontal plane PL2, and thus only the angle in the top view may suffice. Therefore, the line L4 can be used to calculate the joint angle related to the external rotation/internal rotation of the hip joint. Thus, according to the embodiment, as described above, it becomes possible to increase the accuracy of the calculated joint angle related to the external rotation/internal rotation of the hip joint, with respect to the comparative example. As a result of this, according to the embodiment, it becomes possible to increase the accuracy of the calculated ROM of the joint related to the external rotation/internal rotation of the hip joint.

It is noted that, in the example illustrated in FIG. 28 and FIG. 29, the line L4 connecting the centers of gravity of the two non-joint portions, that is to say, the thigh and the anticnemion is used; however, the terminal portion of the foot (an example of the first portion and the second portion) determined from the edge detection may be used, instead of the anticnemion.

Further, in the example illustrated in FIG. 28 and FIG. 29, the external rotation/internal rotation of the hip joint is described; however, the same holds true for the abduction/adduction of the hip joint. Specifically, in the case of the abduction/adduction of the hip joint, the line connecting the centers of gravity of the two non-joint portions, that is to say, the thigh and the anticnemion can be used to calculate the joint angles and the ROM based on the calculated joint angles. Further, in the abduction/adduction of the finger (see No. 18 in FIG. 12), the joint angles and thus the ROM of the joint based on the joint angles can be calculated using a line connecting the centers of gravity of the proximal phalanx and the intermediate phalanx of the finger.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention. Further, all or part of the components of the embodiments described above can be combined.

For example, in the embodiment described above, the targets to be measured by the ROM measurement apparatus 1 include, among the measurement items in "DISPLAY AND MEASUREMENT METHOD OF ROM OF JOINT" illustrated in FIG. 12, the measurement items whose fields of "particular measurement item" are given the circle mark or the mark "x" in FIG. 12. With this arrangement, with respect to the measurement items whose field of "particular measurement item" are given the circle mark or the mark "x", the measurement with the increased accuracy can be implemented using selectively the ordinary joint angle calculation part 121 or the particular joint angle calculation part 122. However, the ROM measurement apparatus 1 may target a part of or all of the particular measurement items whose field of "particular measurement item" are given the circle mark, among the measurement items in "DISPLAY AND MEASUREMENT METHOD OF ROM OF JOINT" illustrated in FIG. 12. In this case, the ROM measurement apparatus dedicated to the particular measurement item (s) can be implemented. In this case, the ordinary joint angle calculation part 121, and the joint position calculation part 1103 of the body portion position calculation part 110 may be omitted. Further, the ROM measurement apparatus 1 may target only one particular measurement item. In this case, the measurement item determination part 112 may be further omitted.

Further, according to the embodiment, the example of the particular measurement items are the measurement items whose field of "particular measurement item" are given the circle mark, among the measurement items in "DISPLAY AND MEASUREMENT METHOD OF ROM OF JOINT" illustrated in FIG. 12. However, the measurement items whose field of "particular measurement item" are given the circle mark, among the measurement items in "DISPLAY AND MEASUREMENT METHOD OF ROM OF JOINT" illustrated in FIG. 12, may be changed if appropriate. In other words, with respect to a part of the measurement items whose field of "particular measurement item" are given the circle mark, among the measurement items in "DISPLAY AND MEASUREMENT METHOD OF ROM OF JOINT" illustrated in FIG. 12, the ordinary joint angle calculation part 121 may be used to calculate the joint angles and the ROM based on the calculated joint angles.

Further, according to the embodiment, the measurement target is the ROM of the joint of the human body; however, the measurement target may be any object with a joint other than the human body such as a robot. Also in this case, the measurement target may be the ROM of the joint of the robot, for example.

Further, according to the embodiment, the centers of gravity of the non-joint portions are used to calculate the joint angle; however, any position other the center of gravity may be used to calculate the joint angle. For example, any position on the skeleton of the non-joint portion may be used instead of the center of gravity of the non-joint portion.

Figure 30:
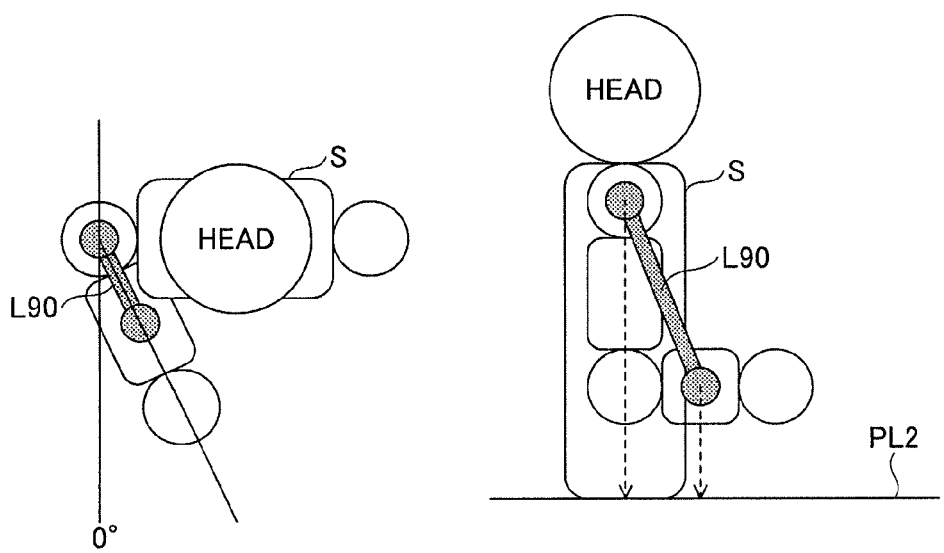
FIG. 30 is a diagram related to a variant, and illustrates top and side views of the test subject in a pose related to the external rotation/internal rotation of the shoulder joint during a measurement session.
Figure 31:
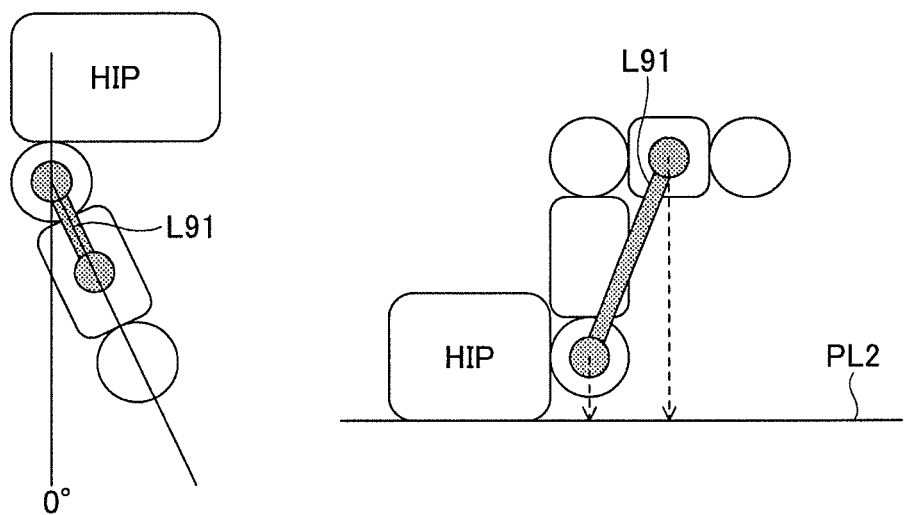
FIG. 31 is a diagram related to a variant, and illustrates top and side views of the test subject in a pose related to the external rotation/internal rotation of the hip joint during a measurement session.

Further, according to the embodiment, with respect to the particular measurement item, the joint angle is calculated using the line connecting the position of the non-joint portion and the position of the non-joint portion or the terminal portion; however, this is not indispensable. As a variant, the joint angle may be calculated using the position of the non-joint portion or the terminal portion of the hand or foot and the position of the joint portion. In the case of the external rotation/internal rotation of the shoulder joint, as illustrated in FIG. 30, a line 90 connecting the center of gravity of the shoulder joint and the center of gravity of the forearm may be projected on the horizontal plane PL2, and the angle between the projected line on the horizontal plane PL2 and the basic axis may be calculated. In this case, instead of the center of gravity of the forearm, the center of gravity of the terminal portion of the hand recognized based on the edge detection may be used. Further, in the case of the external rotation/internal rotation of the hip joint, as illustrated in FIG. 31, a line 91 connecting the center of gravity of the hip joint and the center of gravity of the anticnemion may be projected on the horizontal plane PL2, and the angle between the projected line on the horizontal plane PL2 and the basic axis may be calculated. In this case, instead of the center of gravity of the anticnemion, the center of gravity of the terminal portion of the foot recognized based on the edge detection may be used.

What is claimed is:

1. A measurement apparatus, comprising a processor configured to:
    calculate, based on a distance image of a measurement target object with joints, non-joint portions, and terminal portions, a center of gravity of a first portion which corresponds to a non-joint portion of the measurement target object, and a center of gravity of a second portion which corresponds to a non-joint portion or a terminal portion of the measurement target object and is coupled via a predetermined joint to the first portion; and calculate, based on a first line connecting the centers of gravity of the first and second portions, a joint angle related to a joint of a first measurement target of the measurement target object.

2. The measurement apparatus of claim 1, wherein the joint of the first measurement target is different from the predetermined joint between the first portion and the second portion.

3. The measurement apparatus of claim 2, wherein the measurement target object is a human body of a test subject, and the joint of the first measurement target is closer to a torso than the predetermined joint.

4. The measurement apparatus of claim 1, wherein the processor calculates, as the joint angle, an angle between a basic axis on a reference plane and a projection of the first line projected on the reference plane.

5. The measurement apparatus of claim 1, wherein the processor is further configured to calculate, based on the calculated joint angle, a ROM of the first measurement target.

6. The measurement apparatus of claim 1, wherein the processor is further configured to calculate centers of gravity of two or more joints of the measurement target object, and calculate, based on a second line connecting the centers of gravity of the two or more joints, a joint angle related to a joint of a second measurement target of the measurement target object.

7. The measurement apparatus of claim 6, wherein the processor is further configured to determine a target measurement item, among a plurality of measurement items, wherein the processor calculates the joint angle related to the joint of the first measurement target when the determined target measurement item is a predetermined measurement item, and calculates the joint angle related to the joint of the second measurement target when the determined target measurement item is not the predetermined measurement item.

8. The measurement apparatus of claim 1, wherein the measurement target object is a human body of a test subject, the joint of the first measurement target is a shoulder joint, and the processor calculates the joint angle related to at least one of a flexion/extension of the shoulder joint, an abduction/adduction of the shoulder joint, external rotation/internal rotation of the shoulder joint, and a horizontal flexion/horizontal extension of the shoulder joint.

9. The measurement apparatus of claim 8, wherein the first portion is a brachium, and the second portion is a forearm or a terminal portion of an arm.

10. The measurement apparatus of claim 1, wherein the measurement target object is a human body of a test subject, the joint of the first measurement target is a hip joint, and the processor calculates the joint angle related to at least one of an abduction/adduction of the hip joint, and an external rotation/internal rotation of the hip joint.

11. The measurement apparatus of claim 10, wherein the first portion is a thigh, and the second portion is an anticnemion or a terminal portion of a foot.

12. The measurement apparatus of claim 1, further comprising a distance image sensor configured to obtain the distance image.

13. The measurement apparatus of claim 1, wherein the processor is further configured to recognize, based on a machine learning result, a plurality of portions of the measurement target object from the distance image, the plurality of portions including the first and second portions.

14. A method of measurement, comprising:

using a distance image sensor to obtain a distance image of a measurement target object with joints, non-joint portions, and terminal portions; and using a processor to calculate, based on the distance image, a center of gravity of a first portion which corresponds to a non-joint portion of the measurement target object, and a center of gravity of a second portion which corresponds to a non-joint portion or a target portion of the measurement target object and is coupled via a predetermined joint to the first portion, and calculate, based on a first line connecting the centers of gravity of the first and second portions, a joint angle related to a joint of a first measurement target of the measurement target object.

15. A non-transitory computer-readable recording medium having stored therein a program for causing a computer to execute a process, the process comprising:

inputting a distance image of a measurement target object with joints, non-joint portions, and terminal portions, from a distance image sensor;

calculating, based on the distance image, a center of gravity of a first portion which corresponds to a non-joint portion of the measurement target object, and a center of gravity of a second portion which corresponds to a non-joint portion or a terminal portion of the measurement target object and is coupled via a predetermined joint to the first portion; and calculating, based on a first line connecting the centers of gravity of the first and second portions, a joint angle related to a joint of a first measurement target of the measurement target object.

* * * * *